US010729885B2

(12) United States Patent
Hinman et al.

(10) Patent No.: US 10,729,885 B2
(45) Date of Patent: Aug. 4, 2020

(54) ARTICULATING MECHANISM WITH FLEX-HINGED LINKS

(71) Applicant: Intuitive Surgical Operations, Inc., Sunnyvale, CA (US)

(72) Inventors: Cameron D. Hinman, Woodside, CA (US); David J. Danitz, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 315 days.

(21) Appl. No.: 15/843,855

(22) Filed: Dec. 15, 2017

(65) Prior Publication Data

US 2018/0104448 A1 Apr. 19, 2018

Related U.S. Application Data

(63) Continuation of application No. 14/753,950, filed on Jun. 29, 2015, now Pat. No. 9,861,786, which is a
(Continued)

(51) Int. Cl.
*A61B 17/29* (2006.01)
*A61M 25/01* (2006.01)
*A61B 1/005* (2006.01)

(52) U.S. Cl.
CPC ....... *A61M 25/0138* (2013.01); *A61B 1/0055* (2013.01); *A61B 17/29* (2013.01); *A61M 25/0105* (2013.01)

(58) Field of Classification Search
CPC ............... A61B 17/2804; A61B 17/29; A61B 2017/2926; A61B 2017/2932; A61B 2017/2933; A61B 2017/2938; A61B 2017/2939; A61B 17/0483; A61B 17/0487; A61B 17/08; A61B 17/083; A61B 17/10;
(Continued)

(56) References Cited

U.S. PATENT DOCUMENTS 443,769 A 12/1890 Oliver
1,820,463 A 8/1931 Klein
(Continued)

FOREIGN PATENT DOCUMENTS

CN 1033738 A 7/1989
CN 1148796 A 4/1997
(Continued)

OTHER PUBLICATIONS

Cox J.L., "The Minimally Invasive Maze-III Procedure," Operative Techniques in Thoracic and Cardiovascular Surgery, W.B. Saunders Company, 2000, vol. 5 (1), pp. 79-92.
(Continued)

*Primary Examiner* — Ryan J. Severson
(74) *Attorney, Agent, or Firm* — Haynes and Boone, LLP

(57) ABSTRACT

A surgical clamp comprises a pair of opposing jaws moveable relative to each other between a closed position and first and second open positions. The opposing jaws remain substantially parallel to one another when moving between the closed position and the first open position. The opposing jaws remain non-parallel to one another when moving between the first open position and the second open position.

16 Claims, 10 Drawing Sheets

Related U.S. Application Data continuation of application No. 13/667,755, filed on Nov. 2, 2012, now Pat. No. 9,095,253, which is a continuation of application No. 12/725,377, filed on Mar. 16, 2010, now Pat. No. 8,323,297, which is a continuation of application No. 10/948,911, filed on Sep. 24, 2004, now Pat. No. 7,678,117.

(60) Provisional application No. 60/577,757, filed on Jun. 7, 2004.

(58) Field of Classification Search
CPC . A61B 17/122; A61B 17/128; A61B 17/1285; A61B 2017/0488
See application file for complete search history.

(56) References Cited

U.S. PATENT DOCUMENTS

| | | | |
|---|---|---|---|
| 3,060,972 A | 10/1962 | Sheldon | |
| 3,071,161 A | 1/1963 | Ulrich | |
| 3,190,286 A | 6/1965 | Stokes | |
| 3,266,059 A | 8/1966 | Stelle | |
| 3,557,780 A | 1/1971 | Sato | |
| 3,572,325 A | 3/1971 | Bezell et al. | |
| 3,605,725 A | 9/1971 | Bentov | |
| 4,393,728 A | 7/1983 | Larson et al. | |
| 4,466,649 A | 8/1984 | Ozawa | |
| 4,489,826 A | 12/1984 | Dubson | |
| 4,494,417 A | 1/1985 | Larson et al. | |
| 4,580,551 A | 4/1986 | Siegmund et al. | |
| 4,651,718 A | 3/1987 | Collins et al. | |
| 4,700,693 A | 10/1987 | Lia et al. | |
| 4,763,669 A | 8/1988 | Jaeger | |
| 4,790,294 A | 12/1988 | Allred, III et al. | |
| 4,834,761 A | 5/1989 | Walters | |
| 4,854,626 A | 8/1989 | Duke | |
| 4,880,015 A | 11/1989 | Nierman | |
| 4,984,951 A | 1/1991 | Jameson | |
| 5,005,558 A | 4/1991 | Aomori | |
| 5,174,276 A | 12/1992 | Crockard | |
| 5,257,618 A | 11/1993 | Kondo | |
| 5,271,381 A | 12/1993 | Ailinger et al. | |
| 5,273,026 A | 12/1993 | Wilk | |
| 5,286,228 A | 2/1994 | Lee et al. | |
| 5,297,443 A | 3/1994 | Wentz | |
| 5,314,424 A | 5/1994 | Nicholas | |
| 5,318,589 A * | 6/1994 | Lichtman | A61B 17/29 |
| | | | 600/564 |
| 5,322,064 A | 6/1994 | Lundquist | |
| 5,325,845 A | 7/1994 | Adair | |
| 5,330,502 A | 7/1994 | Hassler et al. | |
| 5,354,162 A | 10/1994 | Burdea et al. | |
| 5,381,782 A | 1/1995 | Delarama et al. | |
| 5,403,342 A | 4/1995 | Tovey et al. | |
| 5,405,344 A | 4/1995 | Williamson et al. | |
| 5,425,743 A | 6/1995 | Nicholas | |
| 5,441,483 A | 8/1995 | Avitall | |
| 5,441,494 A | 8/1995 | Ortiz | |
| 5,454,827 A | 10/1995 | Aust et al. | |
| 5,476,479 A | 12/1995 | Green et al. | |
| 5,486,154 A | 1/1996 | Kelleher | |
| 5,490,819 A | 2/1996 | Nicholas et al. | |
| 5,498,256 A | 3/1996 | Furnish | |
| 5,513,827 A | 5/1996 | Michelson | |
| 5,520,678 A | 5/1996 | Heckele et al. | |
| 5,522,788 A | 6/1996 | Kuzmak | |
| 5,549,636 A | 8/1996 | Li | |
| 5,562,699 A | 10/1996 | Heimberger et al. | |
| 5,570,919 A | 11/1996 | Eusebe | |
| 5,599,151 A | 2/1997 | Daum et al. | |
| 5,609,601 A | 3/1997 | Kolesa et al. | |
| 5,620,415 A | 4/1997 | Lucey et al. | |
| 5,624,398 A | 4/1997 | Smith et al. | |
| 5,626,608 A | 5/1997 | Cuny et al. | |
| 5,632,432 A | 5/1997 | Schulze et al. | |
| 5,643,294 A | 7/1997 | Tovey et al. | |
| 5,647,743 A | 7/1997 | Schmitt | |
| 5,681,263 A | 10/1997 | Flesch | |
| 5,702,408 A | 12/1997 | Wales et al. | |
| 5,704,534 A | 1/1998 | Huitema et al. | |
| 5,713,505 A | 2/1998 | Huitema | |
| 5,716,352 A | 2/1998 | Viola et al. | |
| 5,755,661 A * | 5/1998 | Schwartzman | A61B 17/02 |
| | | | 600/204 |
| 5,759,151 A | 6/1998 | Sturges | |
| 5,762,067 A | 6/1998 | Dunham et al. | |
| 5,772,578 A | 6/1998 | Heimberger et al. | |
| 5,792,164 A | 8/1998 | Lakatos et al. | |
| 5,807,376 A | 9/1998 | Viola et al. | |
| 5,813,813 A | 9/1998 | Daum et al. | |
| 5,823,066 A | 10/1998 | Huitema et al. | |
| 5,827,323 A | 10/1998 | Klieman et al. | |
| 5,836,960 A | 11/1998 | Kolesa et al. | |
| 5,845,540 A | 12/1998 | Rosheim | |
| 5,846,183 A | 12/1998 | Chilcoat | |
| 5,868,760 A | 2/1999 | McGuckin, Jr. | |
| 5,873,817 A | 2/1999 | Kokish et al. | |
| 5,899,425 A | 5/1999 | Corey, Jr. et al. | |
| 5,916,146 A | 6/1999 | Allotta et al. | |
| 5,916,147 A | 6/1999 | Boury | |
| 5,921,956 A | 7/1999 | Grinberg et al. | |
| 5,938,678 A | 8/1999 | Zirps et al. | |
| 5,947,984 A | 9/1999 | Whipple | |
| 5,961,532 A | 10/1999 | Finley et al. | |
| 6,019,722 A | 2/2000 | Spence et al. | |
| 6,050,996 A | 4/2000 | Schmaltz et al. | |
| 6,129,392 A | 10/2000 | Dittrich et al. | |
| 6,161,543 A | 12/2000 | Cox et al. | |
| 6,238,414 B1 * | 5/2001 | Griffiths | A61B 17/29 |
| | | | 606/205 |
| 6,250,532 B1 | 6/2001 | Green et al. | |
| 6,270,453 B1 | 8/2001 | Sakai | |
| 6,446,850 B2 | 9/2002 | Ming-Shun | |
| 6,464,704 B2 | 10/2002 | Schmaltz et al. | |
| 6,471,641 B2 | 10/2002 | Sakamoto | |
| 6,471,696 B1 | 10/2002 | Berube et al. | |
| 6,482,149 B1 | 11/2002 | Torii | |
| 6,491,626 B1 | 12/2002 | Stone et al. | |
| 6,571,042 B1 | 5/2003 | Kordahi | |
| 6,626,824 B2 | 9/2003 | Ruegg et al. | |
| 6,635,071 B2 | 10/2003 | Boche et al. | |
| 6,638,213 B2 | 10/2003 | Ogura et al. | |
| 6,638,287 B2 | 10/2003 | Danitz et al. | |
| RE38,335 E | 11/2003 | Aust et al. | |
| 6,641,528 B2 | 11/2003 | Torii | |
| 6,644,532 B2 | 11/2003 | Green et al. | |
| 6,666,854 B1 | 12/2003 | Lange | |
| 6,669,254 B2 | 12/2003 | Thom et al. | |
| 6,676,676 B2 | 1/2004 | Danitz et al. | |
| 6,682,541 B1 | 1/2004 | Gifford, III et al. | |
| 6,685,715 B2 * | 2/2004 | Danitz | A61B 17/122 |
| | | | 606/157 |
| 6,743,239 B1 | 6/2004 | Kuehn et al. | |
| 6,746,443 B1 | 6/2004 | Morley et al. | |
| 6,749,560 B1 | 6/2004 | Konstorum et al. | |
| 6,752,823 B2 | 6/2004 | Prestel | |
| 6,755,338 B2 * | 6/2004 | Hahnen | A61B 17/07207 |
| | | | 227/175.1 |
| 6,764,445 B2 | 7/2004 | Ramans et al. | |
| 6,773,327 B1 | 8/2004 | Felice et al. | |
| 6,783,491 B2 | 8/2004 | Saadat et al. | |
| 6,817,972 B2 | 11/2004 | Snow | |
| 6,824,548 B2 | 11/2004 | Smith et al. | |
| 6,843,794 B2 | 1/2005 | Sixto, Jr. et al. | |
| 6,858,005 B2 | 2/2005 | Ohline et al. | |
| 6,902,560 B1 | 6/2005 | Morley et al. | |
| 6,942,613 B2 | 9/2005 | Ewers et al. | |
| 6,945,979 B2 | 9/2005 | Kortenbach et al. | |
| 6,960,162 B2 | 11/2005 | Saadat et al. | |
| 6,960,163 B2 | 11/2005 | Ewers et al. | |
| 6,976,969 B2 | 12/2005 | Messerly | |
| 6,994,700 B2 | 2/2006 | Elkins et al. | |
| 7,090,637 B2 | 8/2006 | Danitz et al. | |

(56) References Cited

U.S. PATENT DOCUMENTS

| | | | |
|---|---|---|---|
| 7,108,703 B2 * | 9/2006 | Danitz | A61B 17/122 606/157 |
| 7,138,976 B1 | 11/2006 | Bouzit et al. | |
| 7,410,483 B2 | 8/2008 | Danitz et al. | |
| D583,941 S * | 12/2008 | Leroy | D24/133 |
| 7,480,600 B2 | 1/2009 | Massie et al. | |
| 7,615,066 B2 | 11/2009 | Danitz et al. | |
| 7,678,117 B2 | 3/2010 | Hinman et al. | |
| 7,682,307 B2 | 3/2010 | Danitz et al. | |
| 7,776,065 B2 * | 8/2010 | Griffiths | A61B 17/29 606/207 |
| 7,828,808 B2 | 11/2010 | Hinman et al. | |
| 8,323,297 B2 | 12/2012 | Hinman et al. | |
| 8,419,747 B2 | 4/2013 | Hinman et al. | |
| 8,920,429 B2 | 12/2014 | Hinman et al. | |
| 9,095,253 B2 | 8/2015 | Hinman et al. | |
| 9,517,326 B2 | 12/2016 | Hinman et al. | |
| 9,693,790 B2 * | 7/2017 | He | A61B 17/22031 |
| 10,485,545 B2 * | 11/2019 | Wheeler | A61B 17/0643 |
| 2001/0023313 A1 | 9/2001 | Ide | |
| 2002/0087048 A1 | 7/2002 | Brock et al. | |
| 2002/0096177 A1 | 7/2002 | Toti et al. | |
| 2002/0111604 A1 | 8/2002 | Doyle et al. | |
| 2002/0156497 A1 | 10/2002 | Nagase et al. | |
| 2002/0161281 A1 | 10/2002 | Jaffe et al. | |
| 2002/0177750 A1 | 11/2002 | Pilvisto et al. | |
| 2003/0036748 A1 | 2/2003 | Cooper et al. | |
| 2003/0045900 A1 * | 3/2003 | Hahnen | A61B 17/07207 606/205 |
| 2003/0050649 A1 | 3/2003 | Brock et al. | |
| 2003/0078644 A1 | 4/2003 | Phan | |
| 2003/0109898 A1 | 6/2003 | Schwarz et al. | |
| 2003/0114838 A1 | 6/2003 | ONeill et al. | |
| 2003/0135204 A1 | 7/2003 | Lee et al. | |
| 2003/0149338 A1 | 8/2003 | Francois et al. | |
| 2003/0153902 A1 | 8/2003 | Doyle et al. | |
| 2003/0229271 A1 | 12/2003 | Briscoe et al. | |
| 2003/0233026 A1 | 12/2003 | Saadat et al. | |
| 2004/0054322 A1 | 3/2004 | Vargas | |
| 2004/0138529 A1 | 7/2004 | Wiltshire et al. | |
| 2004/0138700 A1 | 7/2004 | Cooper et al. | |
| 2004/0199052 A1 | 10/2004 | Banik et al. | |
| 2004/0236316 A1 * | 11/2004 | Danitz | A61B 1/0055 606/1 |
| 2005/0090809 A1 | 4/2005 | Cooper et al. | |
| 2005/0096694 A1 | 5/2005 | Lee | |
| 2005/0119527 A1 | 6/2005 | Banik et al. | |
| 2005/0273085 A1 * | 12/2005 | Hinman | A61B 1/0055 606/1 |
| 2006/0009759 A1 | 1/2006 | Chrisitian et al. | |
| 2006/0020287 A1 | 1/2006 | Lee et al. | |
| 2006/0058582 A1 | 3/2006 | Maahs et al. | |
| 2006/0111209 A1 | 5/2006 | Hinman et al. | |
| 2006/0111210 A1 | 5/2006 | Hinman | |
| 2006/0111615 A1 | 5/2006 | Danitz et al. | |
| 2006/0111616 A1 | 5/2006 | Danitz | |
| 2006/0199999 A1 | 9/2006 | Ikeda et al. | |
| 2006/0201130 A1 | 9/2006 | Danitz | |
| 2007/0250113 A1 | 10/2007 | Hegeman et al. | |
| 2007/0287993 A1 | 12/2007 | Hinman et al. | |
| 2008/0255421 A1 | 10/2008 | Hegeman et al. | |
| 2008/0255588 A1 | 10/2008 | Hinman | |
| 2008/0255608 A1 | 10/2008 | Hinman et al. | |
| 2008/0262538 A1 | 10/2008 | Danitz et al. | |
| 2010/0041945 A1 | 2/2010 | Isbell, Jr. | |
| 2010/0234831 A1 * | 9/2010 | Hinman | A61B 1/0055 606/1 |
| 2011/0184459 A1 | 7/2011 | Malkowski et al. | |
| 2013/0060239 A1 * | 3/2013 | Hinman | A61B 1/0055 606/1 |
| 2013/0218141 A1 * | 8/2013 | Hinman | A61B 1/008 606/1 |
| 2015/0297865 A1 | 10/2015 | Hinman et al. | |
| 2018/0104448 A1 * | 4/2018 | Hinman | A61B 1/0055 |

FOREIGN PATENT DOCUMENTS

| | | |
|---|---|---|
| CN | 1163558 A | 10/1997 |
| EP | 0165718 A2 | 12/1985 |
| EP | 0598618 A2 | 5/1994 |
| EP | 0836833 A2 | 4/1998 |
| EP | 1132041 A2 | 9/2001 |
| EP | 0836833 A3 | 9/2002 |
| EP | 1366705 A1 | 12/2003 |
| EP | 1395398 B1 | 1/2006 |
| JP | H06262549 A | 9/1994 |
| JP | 2001299768 A | 10/2001 |
| WO | WO-199849961 A1 | 11/1998 |
| WO | WO-200110292 A1 | 2/2001 |
| WO | WO-0197694 A1 | 12/2001 |
| WO | WO-200213682 A1 | 2/2002 |
| WO | WO-2004019769 A1 | 3/2004 |
| WO | WO-2004105578 A2 | 12/2004 |
| WO | WO-2005067785 A1 | 7/2005 |
| WO | WO-2005120326 A2 | 12/2005 |
| WO | WO-2005120327 A2 | 12/2005 |
| WO | WO-2006057699 A1 | 6/2006 |
| WO | WO-2006057700 A1 | 6/2006 |
| WO | WO-2006057702 A2 | 6/2006 |
| WO | WO-2006073581 A2 | 7/2006 |

OTHER PUBLICATIONS

Danitz, David J.; U.S. Appl. No. 12/766,820 entitled "Articulating mechanism with bifurcating control," filed Apr. 23, 2010.

Danitz, David J,; U.S. Appl. No. 12/766,822 entitled "Articulating catheters," filed Apr. 23, 2010.

Danitz, David J.; U.S. Appl. No. 12/766,825 entitled "Articulating endoscopes," filed Apr. 23, 2010.

Danitz, David J.; U.S. Appl. No. 12/766,827 entitled "Articulating retractors," filed Apr. 23, 2010.

Danitz et al.; U.S. Appl. No. 12/766,818 entitled "Articulating instruments with joystick control," filed Apr. 23, 2010.

Extended European Search Report for Application No. EP13156020, dated Apr. 29, 2013, 6 pages.

Extended European Search Report for Application No. 15173441.5, dated Sep. 21, 2015, 8 pages.

Extended European Search Report for Application No. 15180412.7, dated Jan. 14, 2016, 8 pages.

Hinman, Cameron; U.S. Appl. No. 12/508,478 entitled "Articulating mechanism," filed Jul. 23, 2009.

International Search Report and Written Opinion for Application No. PCT/US2005/018146, dated Dec. 20, 2005, 12 pages.

International Search Report for Application No. PCT/US2005/018145 (WO2005120326), dated Feb. 20, 2006, 5 pages.

Office Action dated Feb. 11, 2014 for Chinese Application No. 201210027026.6 filed May 23, 2005.

Prasad S.M., et al., "Epicardial Ablation on the Beating Heart: Progress Towards an Off-Pump Maze Procedure," The Heart Surgery Forum, Forum Multimedia Publishing, LLC, 2002, vol. 5 (2), pp. 100-104.

Simha P.M., et al., "The Elctrocautery Maze—How I Do It," The Heart Surgery Forum, Forum Multimedia Publishing, LLC, 2001, vol. 4 (4), pp. 340-345.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Written Opinion for Application No. PCT/US2005/018145, dated Feb. 20, 2006, 7 pages.

* cited by examiner

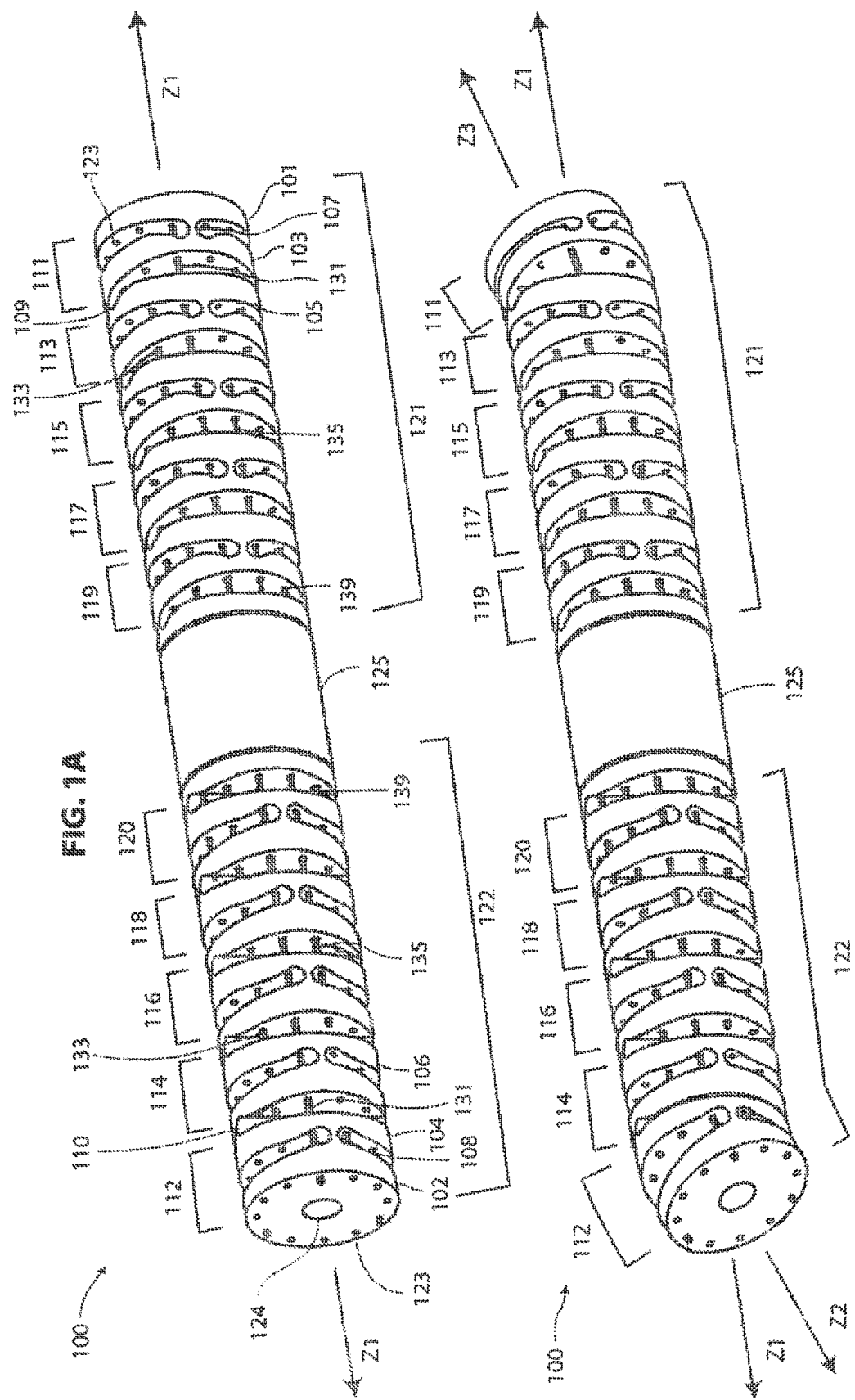

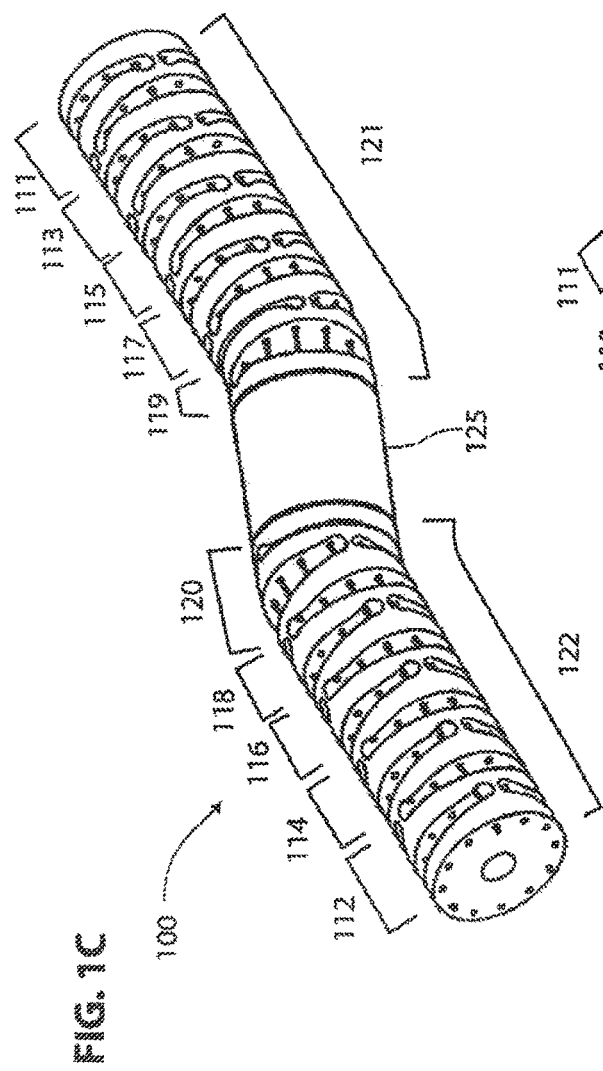
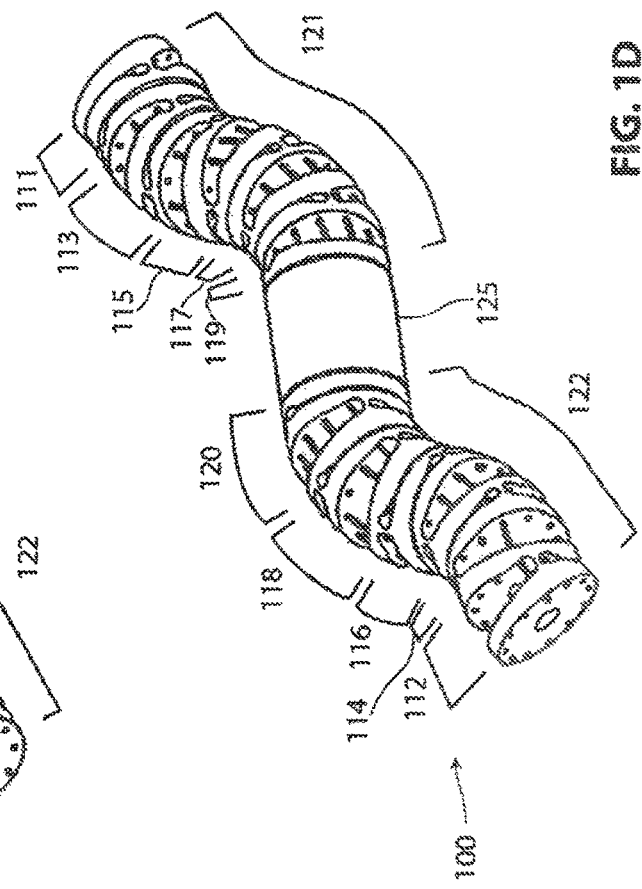

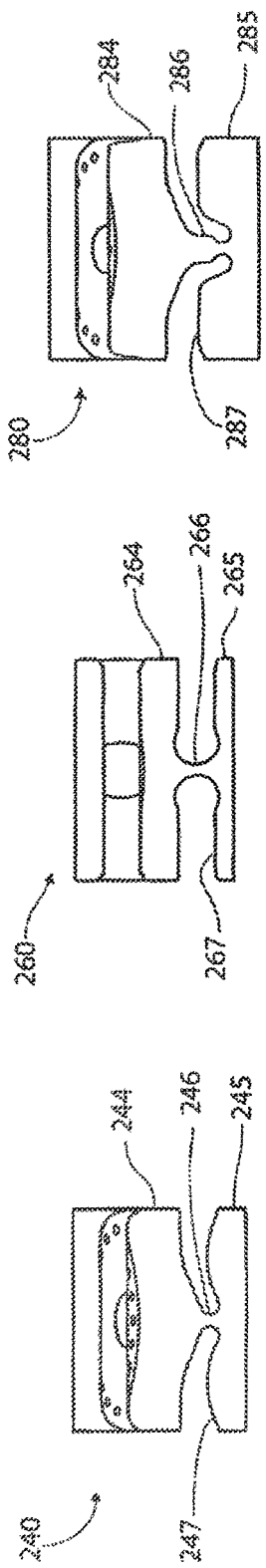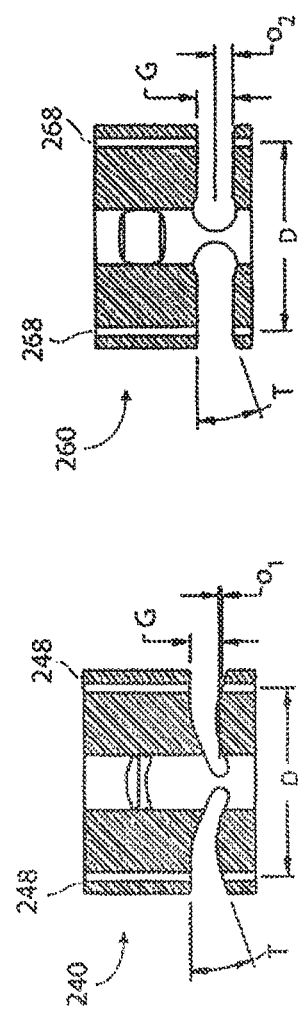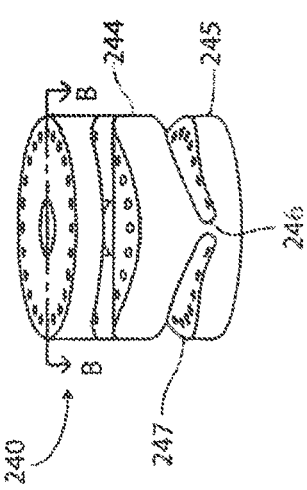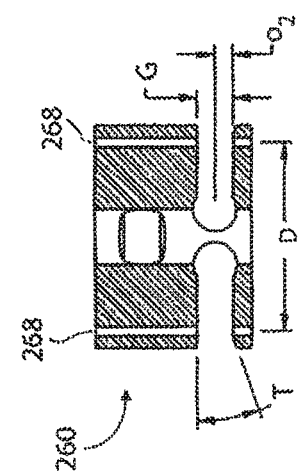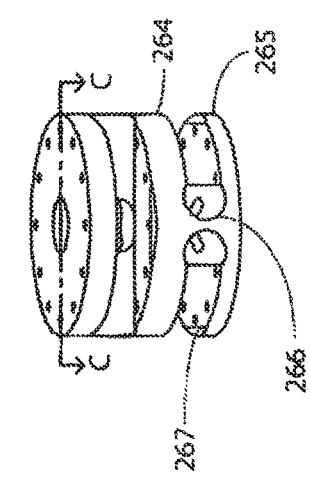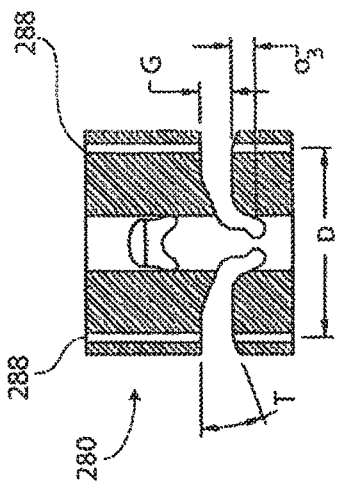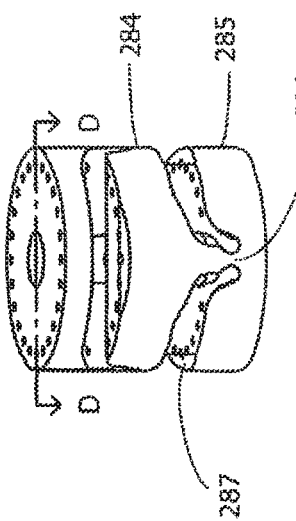

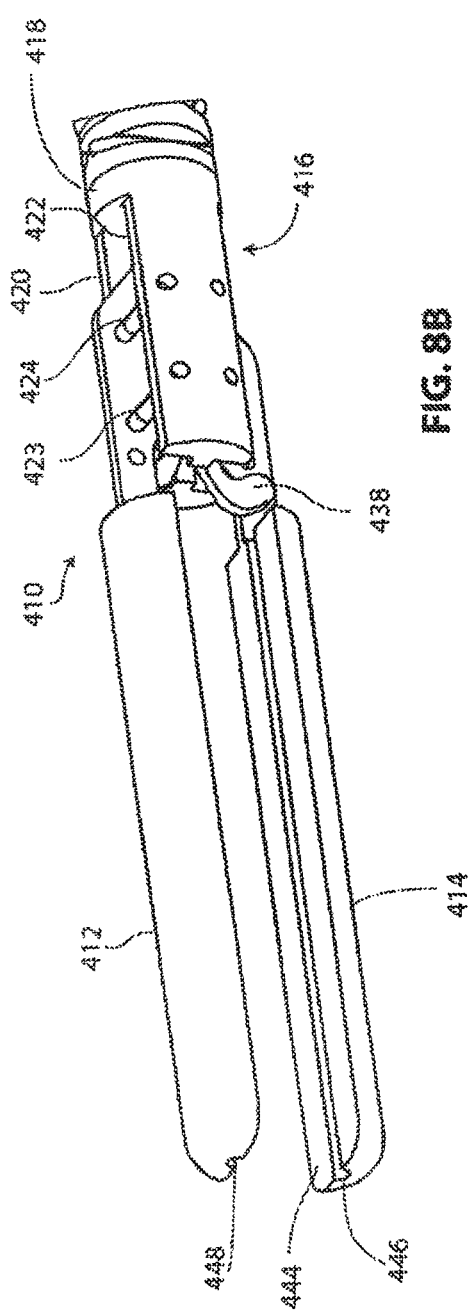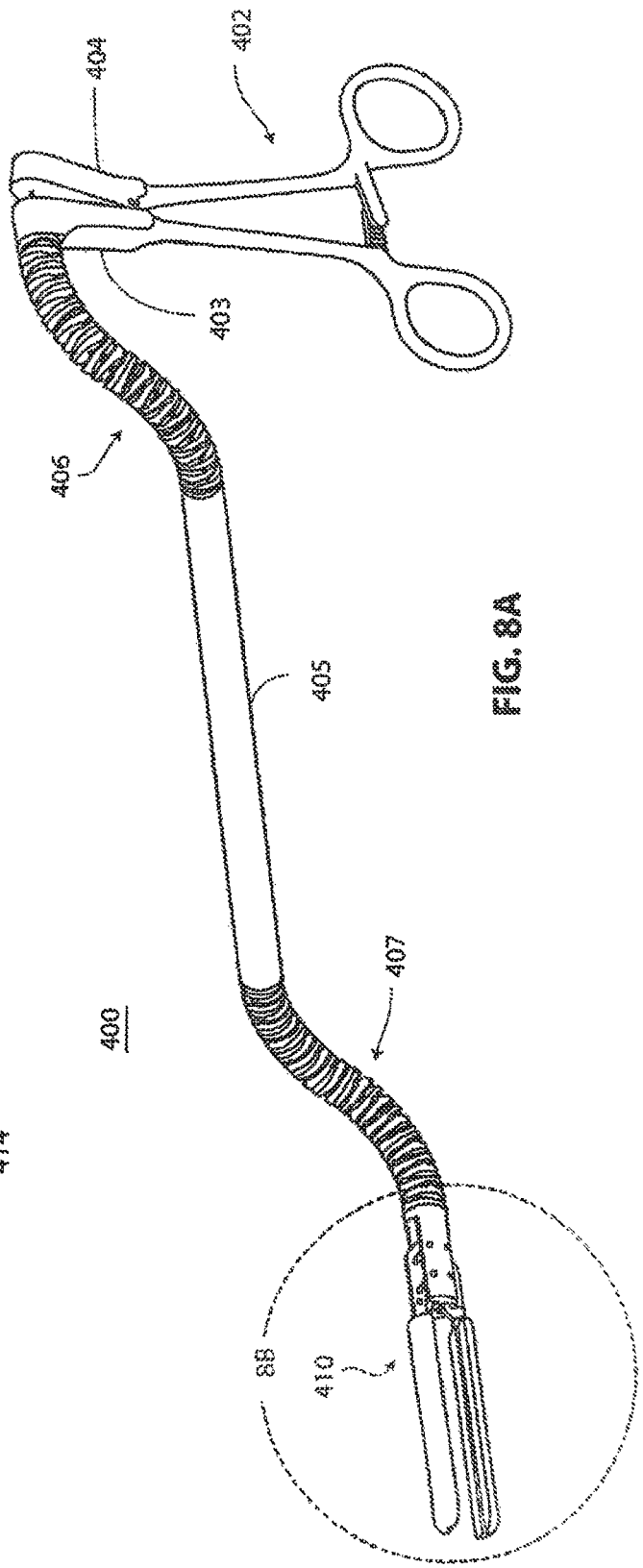
FIG. 8A
FIG. 8B

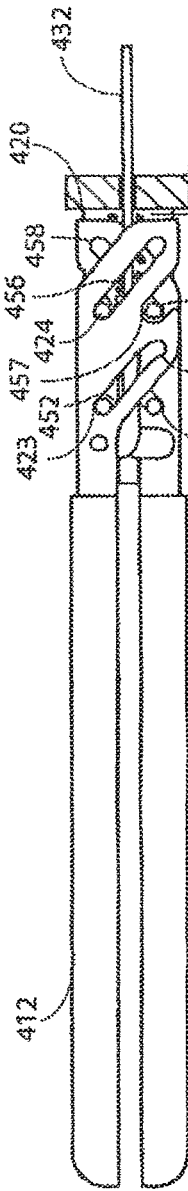

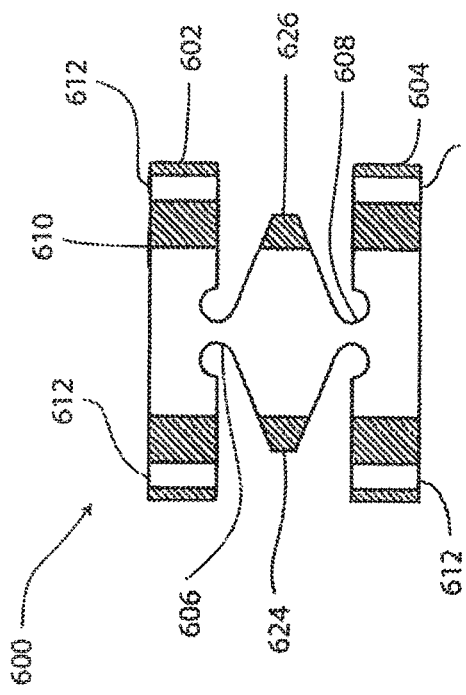
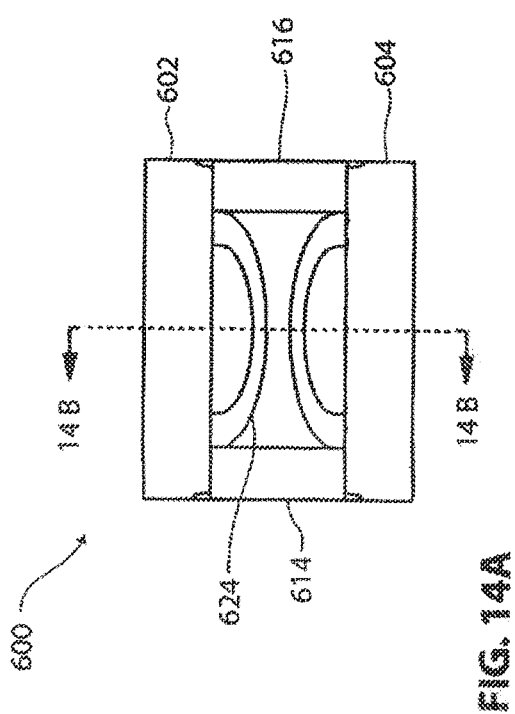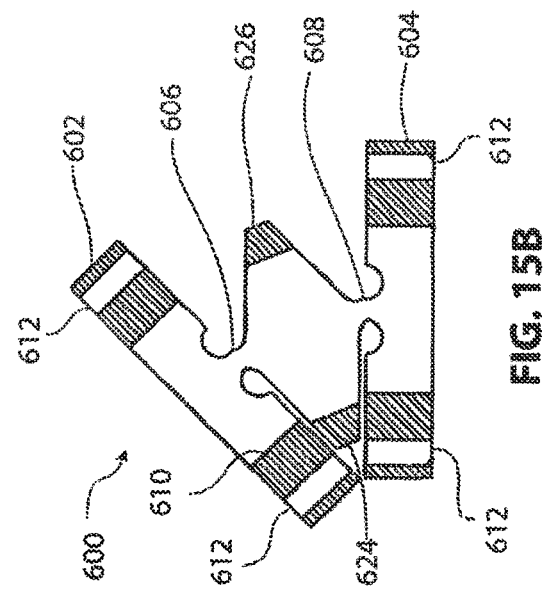
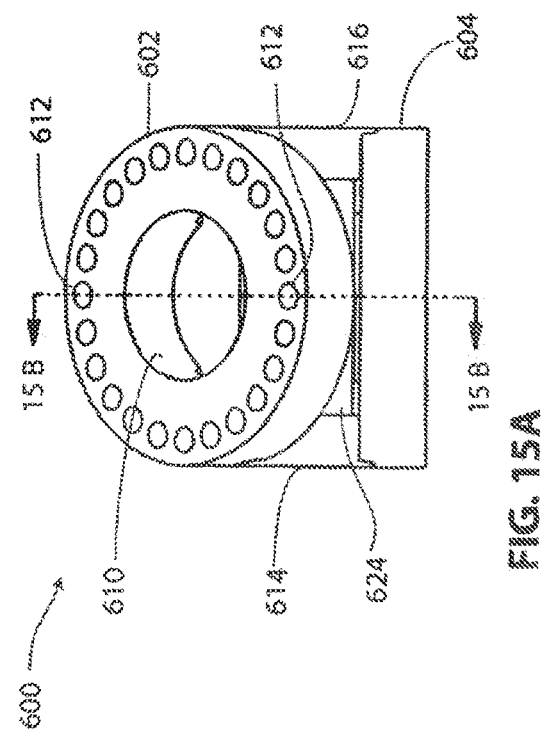

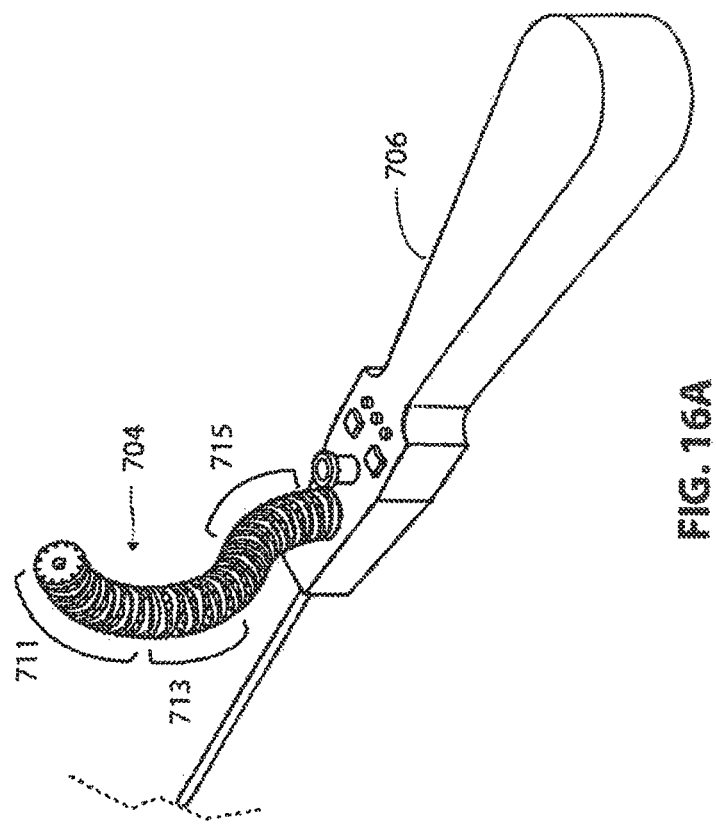
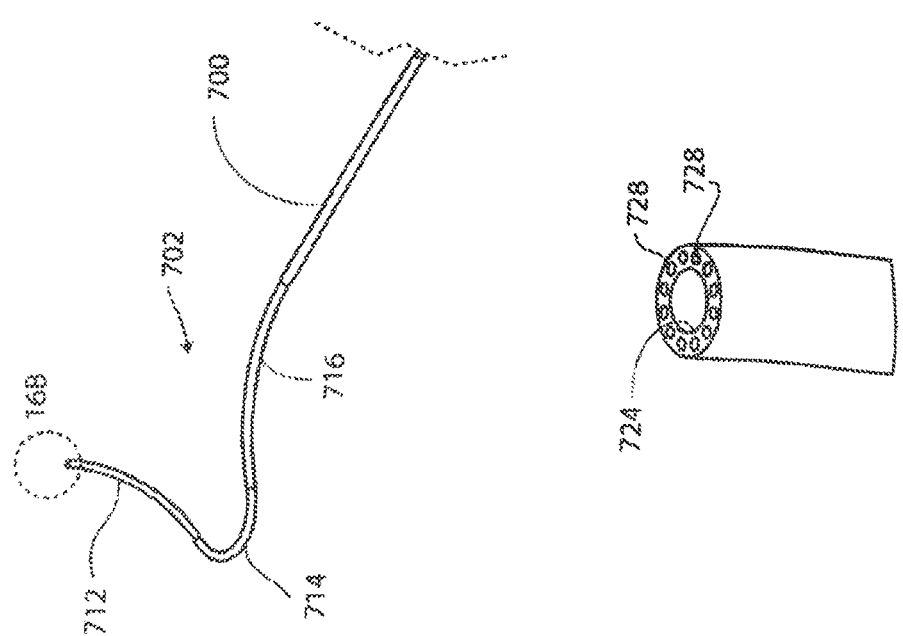
FIG. 16A
FIG. 16B

ARTICULATING MECHANISM WITH FLEX-HINGED LINKS

CROSS REFERENCE TO RELATED APPLICATIONS

This application is a continuation of U.S. patent application Ser. No. 14/753,950, filed on Jun. 29, 2015, which is a continuation of U.S. patent application Ser. No. 13/667,755, filed on Nov. 2, 2012, which is a continuation of U.S. patent application Ser. No. 12/725,377, filed on Mar. 16, 2010, which is a continuation of U.S. patent application Ser. No. 10/948,911, filed on Sep. 24, 2004, issued as U.S. Pat. No. 7,678,117 on Mar. 16, 2010, which claims benefit of U.S. Provisional Application No. 60/577,757, filed Jun. 7, 2004. The contents of each of the above listed applications are hereby incorporated by reference into the present disclosure in their entireties.

BACKGROUND OF THE INVENTION

This invention relates to articulating mechanisms and applications thereof including the remote steering, guidance and/or manipulation of instruments and tools.

The ability to easily remotely steer, guide and/or manipulate instruments and tools is of interest in a wide variety of industries and applications, in particular where it is desired to navigate an instrument or tool into a workspace that is not easy to manually navigate by hand or that might otherwise present a risk or danger. These can include situations where the targeted site for the application of a tool or instrument is difficult to access, e.g. certain surgical procedures, or the manufacture or repair of machinery, or even commercial and household uses, where manual access to a targeted site is restricted or otherwise. Other situations can include e.g. industrial applications where the work environment is dangerous to the user, for example, workspaces exposed to dangerous chemicals. Still other situations can include e.g. law enforcement or military applications where the user may be at risk, such as deployment of a tool or instrument into a dangerous or hostile location.

Using surgical procedures as an illustrative example, procedures such as endoscopy and laparoscopy typically employ instruments that are steered within or towards a target organ or tissue from a position outside the body. Examples of endoscopic procedures include sigmoidoscopy, colonoscopy, esophagogastroduodenoscopy, and bronchoscopy. Traditionally, the insertion tube of an endoscope is advanced by pushing it forward, and retracted by pulling it back. The tip of the tube may be directed by twisting and general up/down and left/right movements. Oftentimes, this limited range of motion makes it difficult to negotiate acute angles (e.g., in the rectosigmoid colon), creating patient discomfort and increasing the risk of trauma to surrounding tissues. Laparoscopy involves the placement of trocar ports according to anatomical landmarks. The number of ports usually varies with the intended procedure and number of instruments required to obtain satisfactory tissue mobilization and exposure of the operative field. Although there are many benefits of laparoscopic surgery, e.g., less postoperative pain, early mobilization, and decreased adhesion formation, it is often difficult to achieve optimal retraction of organs and maneuverability of conventional instruments through laparoscopic ports. In some cases, these deficiencies may lead to increased operative time or imprecise placement of components such as staples and sutures. Steerable catheters are also well known for both diagnostic and therapeutic applications. Similar to endoscopes, such catheters include tips that can be directed in generally limited ranges of motion to navigate a patient's vasculature.

There have been many attempts to design endoscopes and catheters with improved steerability. For example, U.S. Pat. No. 3,557,780 to Sato; U.S. Pat. No. 5,271,381 to Ailinger et al.; U.S. Pat. No. 5,916,146 to Alotta et al.; and U.S. Pat. No. 6,270,453 to Sakai describe endoscopic instruments with one or more flexible portions that may be bent by actuation of a single set of wires. The wires are actuated from the proximal end of the instrument by rotating pinions (Sato), manipulating knobs (Ailinger et al.), a steerable arm (Alotta et al.), or by a pulley mechanism (Sato). U.S. Pat. No. 5,916,147 to Boury et al. discloses a steerable catheter having four wires that run within the catheter wall. Each wire terminates at a different part of the catheter. The proximal end of the wires extend loosely from the catheter so that the physician may pull them. The physician is able to shape and thereby steer the catheter by selectively placing the wires under tension.

Although each of the devices described above are remotely steerable, their range of motion is generally limited. The steering mechanisms may also be laborious to use, such as in the catheter of Boury et al. where each wire must be separately pulled to shape the catheter. Further, in the case of e.g. endoscopes and steerable catheters that use knob and pulley mechanisms, it requires a significant amount of training to become proficient in maneuvering the device through a patient's anatomy.

Consequently, a device with enhanced remote maneuverability to controllably navigate complex geometries may allow more efficient and precise advancement and deployment of instruments and tools. It would also be advantageous for such a device to provide a more intuitive and facile user interface to achieve such enhanced maneuverability. Such a device would have widespread application in guiding, steering and/or manipulating instruments and tools across numerous industries. Such a device would also of itself have entertainment, recreation and educational value.

BRIEF SUMMARY OF THE INVENTION

The present invention provides articulating mechanisms and components thereof useful for a variety of purposes including but not limited to the remote manipulation of instruments and tools. Such instruments and tools can include surgical or diagnostic instruments or tools, including but not limited to endoscopes, light sources, catheters, Doppler flow meters, microphones, probes, retractors, dissectors, staplers, clamps, graspers, scissors or cutters, ablation or cauterizing elements, and the like. Other instruments or tools in non-surgical applications include but are not limited to graspers, drivers, power tools, welders, magnets, optical lenses and viewers, light sources, electrical tools, audio/visual tools, lasers, monitors, and the like. Depending on the application, it is contemplated that the articulating mechanisms and components of the present invention can be readily scaled to accommodate the incorporation of or adaptation to numerous instruments and tools. The articulating mechanism may be used to steer these instruments or tools to a desired target site, and can further be employed to actuate or facilitate actuation of such instruments and tools.

In one variation of the invention, an articulating mechanism is provided that includes multiple pairs of flexible segments, with each flexible segment of each pair being maintained in a spaced apart relationship relative to the other flexible segment of the pair. The flexible segments comprise a unit of at least one link and at least one flexible hinge, with adjacent flexible segments in the mechanism joined by flexible hinges. The mechanism further includes at least one set of cables connecting the flexible segments of at least one discrete pair to one another, such that movement of one flexible segment of the connected pair causes corresponding relative movement of the other flexible segment of the pair. In further variations, additional cable sets are provided that connect the flexible segments of additional discrete pairs. The flexible segments can form proximal and distal ends of the mechanism where movement of the proximal end of the articulating mechanism results in corresponding relative movement of the distal end. For movement in two dimensions, the flexible hinges are aligned in parallel. For movement in three dimensions, at least one flexible hinge of the mechanism is oriented at an acute angle to at least one other flexible hinge of the mechanism. For maximum range of motion in three dimensions, at least one flexible hinge is oriented orthogonal to at least one other flexible hinge.

In another variation of the invention, flexible members for use in articulating mechanisms are provided. The flexible members will include one or more flexible segments joined together. The flexible members can be formed with any number of flexible segments and can further be provided with reciprocal means for axially connecting the members together in lengthwise fashion. The flexible members can be used to form an articulating mechanism according to the present invention, or alternatively, can be incorporated into other mechanisms and devices. In one variation, flexible member includes flexible hinges are oriented in parallel. In another variation, the flexible members include at least one flexible hinge that is oriented at an acute angle to at least one other flexible hinge. In a further variation, at least one flexible hinge is oriented orthogonal to at least one other flexible hinge.

In further variations of the invention, flexible segments are provided that can form or be incorporated into flexible members or articulating mechanisms according to the invention. The flexible segments comprise a unit of at least one link and at least one flexible hinge. In certain variations, these flexible segments are designed with flexible hinges that bend or flex at particular predetermined positions, the locations of which will have particular effects on cables running through the segments. In particular, these predetermined positions will have an impact on the relative tautness of cables passing through the flexible segments. This impact, also referred to as cable pull bias, can be negative, neutral or positive. In one aspect, the predetermined flex position provides for a negative cable pull bias where one or more cables passing through adjacent flexible segments will develop slack when the mechanism is bent or articulated. In another aspect, the predetermined flex position provides a neutral cable pull bias, where cable slack is reduced or eliminated when the mechanism is bent or articulated. In yet another aspect, the predetermined flex position provides a positive cable pull bias where one or more cables associated with the flexible segment will have increased tension when the mechanism is bent or articulated. Each of these configurations may have advantages depending on the particular application at hand.

In further aspects of the invention, a tool or instrument may be attached to and extend from the distal end of the articulating mechanisms, or the articulating mechanisms may be otherwise incorporated into such instruments or tools. In the case of surgical applications, examples of surgical or diagnostic tools include, but are not limited to, endoscopes, light sources, catheters, Doppler flow meters, microphones, probes, retractors, dissectors, staplers, clamps, graspers, scissors or cutters, and ablation or cauterizing elements. For other applications, numerous tools or instruments are likewise contemplated, including without limitation, e.g., graspers, drivers, power tools, welders, magnets, optical lenses and viewers, electrical tools, audio/visual tools, lasers, light sources, monitors, and the like. The types of tools or instruments, methods and locations of attachment, and applications and uses include, but are not limited to, those described in pending and commonly owned U.S. application Ser. Nos. 10/444,769 and 10/928,479, incorporated herein by reference in their entirety.

BRIEF DESCRIPTION OF THE DRAWINGS

FIGS. 1A-1D show perspective views of an articulating mechanism according to one embodiment of the invention, with pairs of flexible segments connected by corresponding cable sets and having flexible hinges oriented orthogonal to one another. FIG. 1A shows the mechanism in its natural, unactuated configuration. FIGS. 1B-1D show the mechanism in different states of manipulation.

FIGS. 3A and 3B are perspective and side views, respectively, of a flexible member according to yet another embodiment of the invention. FIG. 3C is a cross-sectional view of the flexible member of FIG. 3A, taken along the plane designated by line B-B.

FIGS. 4A and 4B are perspective and side views, respectively, of a flexible segment according to a further embodiment of the invention. FIG. 4C is a cross-sectional view of the flexible segment of FIG. 4A, taken along the plane designated by line C-C.

FIGS. 5A and 5B are perspective and side views, respectively, of a flexible segment according to yet another embodiment of the invention. FIG. 5C is a cross-sectional view of the flexible segment of FIG. 5A, taken along the plane designated by line D-D.

FIG. 8A is a perspective view of a surgical instrument incorporating a grasping tool and an articulating mechanism according to an embodiment of the invention. FIG. 8B is an enlarged view of the distal end of the instrument of FIG. 8A, showing the grasping tool in greater detail.

FIGS. 9A and 9B show end and cross-sectional views, respectively, of the grasping tool depicted in FIG. 8B in the closed position, with the cross-sectional view of FIG. 9B taken along the plane designated by line 9B-9B in FIG. 9A.

FIGS. 10A and 10B show end and cross-sectional views, respectively, of the grasping tool depicted in FIG. 8B in a first open position (with the jaws remaining parallel) with the cross-sectional view of FIG. 10B taken along the plane designated by line 10B-10B in FIG. 9A.

FIGS. 11A and 11B show end and cross-sectional views, respectively, of the grasping tool depicted in FIG. 8B in a second open position (with the jaws having moved to a non-parallel position) with the cross-sectional view of FIG. 10B taken along the plane designated by line 10B-10B in FIG. 9A.

FIGS. 14A and 14B show side and cross-sectional views, respectively, of a flexible segment according to further embodiment of the invention, in a straight, unbent configuration. The cross-sectional view of FIG. 14B is taken along the line designated 14B-14B in FIG. 14A.

FIGS. 15A and 15B show side and cross-sectional views, respectively, of the flexible segment FIGS. 14A-14B, in a bent configuration. The cross-sectional view of FIG. 15B is taken along the line designated 15B-15B in FIG. 15A.

FIG. 16A is a perspective view of a catheter incorporating a an articulating mechanism according to an embodiment of the invention. FIG. 16B is an enlarged view of the distal end of the catheter of FIG. 16A.

DETAILED DESCRIPTION OF THE INVENTION

Figure 2C:
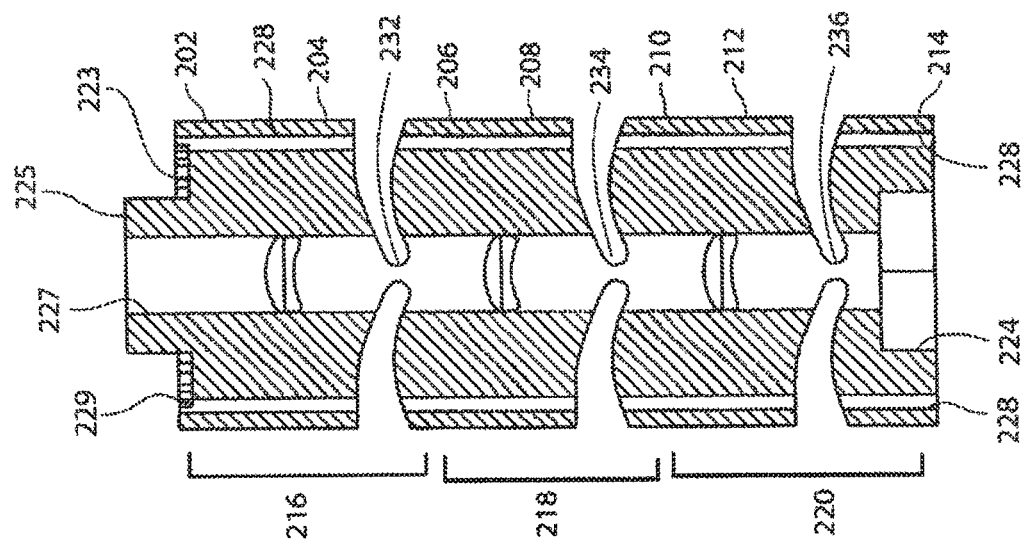
FIG. 2C is a cross-sectional view of the flexible segment as shown in FIG. 2B, taken along the plane designated by line A-A.

Articulating mechanisms according to the invention generally include multiple pairs of flexible segments and at least one set of cables connecting at least one discrete pair of flexible segments. In certain embodiments, the articulating mechanisms can be formed of flexible members that are made of flexible segments and that can have varying numbers of links. The term "link" as used herein refers to a discrete portion of the mechanism, flexible member, or flexible segment that is capable of movement relative to another discrete portion of the mechanism, flexible member or flexible segment. Links are typically, but need not be, cylindrical. The links are generally aligned along the longitudinal axis of the mechanism, flexible member or flexible segment. Adjacent links of the mechanism, flexible member or flexible segment are joined by flexible hinges. Terminal links of the articulating mechanism, flexible member or flexible segment can also be secured to or incorporated into other aspects of the mechanism or tools attached to the mechanism. The term "flexible hinge" refers to a discrete section that extends from a link and is capable of flexure. Flexible hinges are typically, but need not be, oriented perpendicular to the longitudinal axis of the mechanism, flexible member or flexible segment. Links and flexible hinges are typically, but not necessarily, integrally formed together. A "flexible segment" usually includes one or more adjacent links connected by flexible hinges. A flexible segment capable of movement in two dimensions with a single degree of freedom can have a single flexible hinge that connects two links. A flexible segment capable of movement in three dimensions with two degrees of freedom can have two flexible hinges oriented at an acute angle to one another connecting to three links. For a maximum three-dimensional range of motion, the angle will be orthogonal. Flexible segments can provide the component pieces of a flexible member or of an articulating mechanism. A "flexible segment pair" refers to a flexible segment at one end of the mechanism that corresponds to another flexible segment at the opposite end of the mechanism. Articulating mechanisms according to the invention will include a plurality of flexible segments that are members of discrete pairs. The flexible segments are generally arranged to form a proximal end and a distal end, with one flexible segment of each pair being situated at the proximal end, and the other flexible segment at the distal end. In order to achieve the greatest freedom of motion in three dimensions, at least one flexible hinge of the mechanism is oriented orthogonal to at least one other hinge of the mechanism. However, the invention also contemplates configurations where flexible hinges are oriented parallel or are offset at any acute angle.

A cable set can connect the flexible segments of a discrete pair to one another so that movement of one flexible segment of a pair causes a corresponding movement of the other flexible segment of the pair. As used herein, the term "active flexible segment" or "active flexible segment pair" refers to flexible segments that are directly connected to one another by a cable set. The term "spacer flexible segment" or "spacer flexible segment pair" refers to flexible segments that are not directly connected by a cable set. Spacer flexible segments can nevertheless be disposed between active flexible segments and provide for the passage of cable sets that connect active flexible segments. The ability to manipulate active flexible segment pairs allows for the mechanism to readily form complex three-dimensional configurations and geometries as is further detailed herein. With conventional articulating devices that rely on cable sets or wires that pass through otherwise unconnected links, it is difficult to obtain such complex geometries because such devices are typically designed such that the steering cables or wires pass through each link and terminate at a distal-most link. Thus, all the segments bend together in a coordinated response to movement of the wire or cable set, typically in a curved, or arcuate fashion.

In addition to the formation of complex configurations, the present invention also allows for increased rigidity of the mechanism by constraining manipulated active flexible segments and allowing such segments to resist movement due to laterally applied forces. A given flexible segment pair is considered fully constrained if upon manipulating the segment pair to achieve the desired shape, and fixing one segment of the pair in that desired shape, the other segment of the pair can resist loads while maintaining its desired, unloaded shape. A minimum of two cables are required to fully constrain a single degree of freedom flexible segment that has two links and one flexible hinge. For a two degree of freedom flexible segment having three links and two flexible hinges (oriented either at an acute angle or orthogonally to one another) a minimum of three cables are required to fully constrain the segment. This is not always the case with conventional articulating devices. Spacer flexible segments will not be so constrained, and the inclusion of such unconstrained spacer flexible segments may be advantageous in many situations where it is desirable to have portions of the actuated mechanism be less rigid The terms "instrument" and "tool" are herein used interchangeably and refer to devices that are usually handled by a user to accomplish a specific purpose. For purposes of illustration only, articulating mechanisms of the invention will be described in the context of use for the remote guidance, manipulation and/or actuation of surgical or diagnostic tools and instruments in remote accessed regions of the body. As previously noted, other applications of the articulating mechanism besides surgical or diagnostic applications are also contemplated and will be apparent to one of skill in the art. Generally any such application will include any situation where it is desirable to navigate an instrument or tool into a workspace that is not easy to manually navigate by hand or that might otherwise present a risk or danger. These include, without limitation, industrial uses, such as for the navigation of a tool, probe, sensor, etc. into a constricted space, or for precise manipulation of a tool remotely, for example, for the assembly or repair of machinery. These can also include commercial and household situations where the targeted site for the application of a tool or instrument is difficult to access. Other situations can include e.g. industrial applications where the work environment is dangerous to the user, for example, workspaces exposed to dangerous chemicals. Still other situations can include e.g. law enforcement or military applications where the user may be at risk, such as deployment of a tool or instrument into a dangerous or hostile location. Yet other uses include applications where simply remote manipulation of complex geometries is desirable. These include uses in recreation or entertainment, such as toys or games, e.g., for remote manipulations of puppets, dolls, figurines, and the like.

Turning to the embodiment shown in FIGS. 1A-ID, articulating mechanism 100 includes a plurality of flexible segments that form a proximal end 121 and a distal end 122. Flexible segments 111 and 112, 113 and 114, 115 and 116, 117 and 118 and 119 and 120, respectively, are each members of a discrete pair, with one flexible segment of a pair (111, 113, 115, 117 or 119) at proximal end 121 with the other (112, 114, 116, 118 or 120) at distal end 122. As depicted, flexible segment 111 at proximal end 121 is formed of links 101, 103 and 105 connected by flexible hinges 107 and 109 oriented orthogonal to each other. Cable channels 123 are located and pass through the periphery of each link for accepting passage and connection of cable sets. The flexible segment also includes central channel 124 running through the longitudinal axis of the flexible segment to accommodate additional cables, wires, fiberoptics or other like elements associated with a desired tool or instrument used in conjunction with the mechanism. Paired flexible segment 112 at distal end 122 similarly is formed of links 102, 104 and 106 connected by flexible hinges 108 and 110 oriented orthogonal to one another and likewise including similar cable channels and central channel. The remaining flexible segments of both the proximal end (113, 115, 117 and 119) and distal end (114, 116, 118 and 120) have the same configuration with the last link of one segment also functioning as the first link of the next segment. And as shown, each flexible hinge is oriented orthogonal to adjacent hinges. As previously noted flexible segments of such configuration move in two degrees of freedom and are moveable in three dimensions. The proximal flexible segments (111, 113, 115 and 119) are connected to the distal flexible segments (112, 114, 116 and 120) by sets of cables 131, 133, 135 and 139, respectively. These flexible segment pairs are thus active flexible segments. Flexible segments 117 and 118 are not directly connected by a cable set and thus function as spacer segments. The mechanism further includes spacer element 125 disposed between the proximal end 121 and the distal end 122 to provide additional separation between the proximal flexible segments and distal flexible segments. The spacer element is optional, and may be of any length appropriate to the intended application. It is configured to accommodate all the cables that connect the flexible segment pairs, as well as additional cables, wires, fiberoptics or other like elements associated with a desired tool or instrument used in conjunction with the mechanism.

Each active flexible segment at the proximal end of the articulating mechanism is connected to its corresponding active flexible segment at the distal end by two or more cables. Each cable set may be made up of at least two cables. As noted, movement of one active flexible segment pair is controlled by its corresponding cable set and is independent of any other flexible segment pair. In certain variations, for example, a cable set will include three cables spaced 120 degrees apart. By using a set of three cables to connect an active flexible segment having at least one flexible hinge oriented orthogonal to at least one other flexible hinge, each active flexible segment pair can be manipulated or moved in three degrees of freedom, independently of any other active pairs. These three degrees of freedom include up/down motion, left/right motion, and rotational or "rolling" motion. By combining a plurality of active flexible segments, multiple degrees of freedom are achieved, allowing the articulating mechanism to be shaped into various complex configurations. For example, the variation shown in FIGS. 1A-1D has a total of four active flexible segment pairs each independently connected by sets of three cables each, for possible motion in twelve degrees of freedom. Such multiple degrees of freedom are not available in typical conventional mechanisms where only a single set of cables is employed to manipulate the mechanism links.

As noted the flexible segments also include a plurality of channels for passage of the cables that connect active flexible segment pairs, as shown. Cables, wires, fiberoptics, flexible endoscopes and the like, may also be run through a central channel provided in the flexible segments, if desired. Channels can also be provided to allow for passage of fluid delivery tubes. The flexible segments can further be designed with attachment channels that communicate with the flexible segment exterior for mounting other elements, e.g., energy sources (for ablation or coagulation) or fiberoptics, or flexible endoscopes, at the distal end of the articulating mechanism. More than one flexible segment may include an attachment channel so that the attachment channel may extend from the distal end to the proximal end of the mechanism.

Referring to FIG. 1A, cables fixed to a proximal active flexible segment travel through spacer 125 to connect with a corresponding distal flexible segment of the pair. As shown in FIGS. 1B-1C, movement of active proximal flexible segments results in inverted, reciprocal movement of active distal flexible segments. In other variation, the cables can be twisted or rotated 180 degrees while running through spacer element 125 so that the reciprocal movement at the distal end 122 is mirrored. The articulating mechanisms of this invention may be configured to include cables twisted in any amount between 0 degrees to 360 degrees to provide for 360 degree range of reciprocal motion.

Spacer flexible segments, i.e., flexible segments not connected by discrete sets of cables (e.g., 117 and 118 in FIGS. 1A-ID), may also be included in the articulating mechanisms. These flexible segments can be inserted between active flexible segments at either the proximal or distal ends or both, and act as flexible segments that are not independently actuatable, but that do allow for pass through of cable sets to neighboring active flexible segments. Spacer flexible segments can be desirable for providing additional length to the proximal and/or distal end of the mechanism. In addition the inclusion of spacer flexible segments (or a greater relative number of spacer flexible segments) at one end of the mechanism, allows for the proportional scaling of movement or motion of the corresponding other end. For example, the inclusion of spacer flexible segments (or a greater relative number of spacer flexible segments) at the proximal end would require a more exaggerated movement by the user at the proximal end to achieve the desired motion at the distal end. This could be advantageous in situations where fine, delicate controlled movements were desired, such as, for example, situations where there is a risk that a user may not possess the necessary dexterity to perform the desired procedure absent such proportional scaling of the distal end movement or motion. Alternatively, spacer flexible segments (or a greater relative number of spacer flexible segments) could be provided on the distal end, in which case the degree of distal end movements would be proportionally greater than those of the proximal end, which may also be desirable for particular applications. In addition to the above, proportional scaling of movement or motion can also be accomplished by increasing or decreasing the cable channel pattern radius of the flexible segments, either active or spacer, at either the proximal or distal end, as will be further detailed herein.

Complex movements, including up, down, right, left, oblique, and rotational movements, may be accomplished due to the formation of pairs of active flexible segments connected by discrete cable sets, as described above. For example, in the variation shown in FIG. 1B, the most distal active flexible segment 112 at the distal end may be actuated, while all other flexible segments remain stationary, by actuation of the most proximal flexible segment 111 at the proximal end. Proximal segment 111 can further be manipulated such that distal-most flexible segment 112 sweeps a right circular cone about longitudinal axis Z1 of the mechanism, the base diameter of which increases with such factors as increased length of the flexible hinge, enhanced cable flexibility, and addition of spacer flexible segments between flexible segment 112 and the next adjacent active flexible segment. As, if not more, importantly, proximal segment 111 can be rotated or "rolled" about its axis, represented as Z3 in FIG. 1B, and the resultant torque transmitted through the mechanism to distal segment 112, such that segment 112 rotates about its axis, represented as Z2 in FIG. 1B.

As shown in FIG. 1C, the most proximal active flexible segment at the distal end, 120, is actuated while all other flexible segments remain stationary by actuating only the moat distal active flexible segment at the proximal end, flexible segment 119. By manipulating the proximal and in this configuration, the distal end can sweep a right circular cone with a larger base diameter than that discussed above with respect to FIG. 1B, due to the increased number of segments distal to the actuated segment. Again, the proximal end can be rotated or "roiled" about its axis and the resultant torque transmitted through the mechanism to the distal end.

Although a number of segment movements are depicted in FIGS. 1B-1D, other complex, 3-dimensional movements incorporating up, down, right, left, oblique and rotational movements, may also be accomplished. For example, FIG. 1D shows the distal end 122 of articulating mechanism 100 having multiple curvatures along its length, each oriented in directions independent of one another. As noted, articulating mechanism 100 of FIG. 1A-ID has four active pairs of flexible segments, each of which is connected by a cable set having three cables, providing for movement in twelve degrees of freedom, but other configurations of flexible segment pairs and cable sets will readily achieve similar complex movements and geometries. The ability of portions the mechanism to bend in different directions at the same time and create active complex configurations is provided by the independent actuation of each active flexible segment pair as controlled through its corresponding cable set.

Figure 2B:
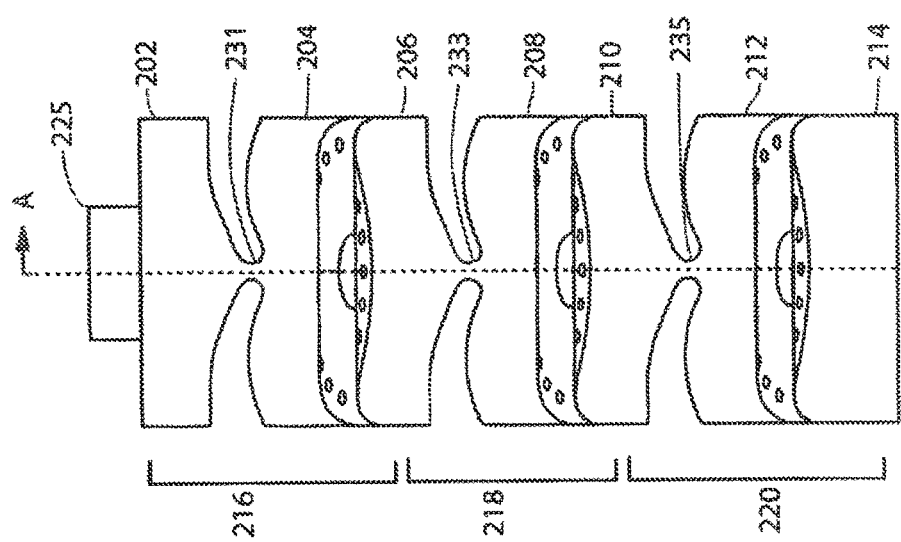
FIG. 2B is a side view of the flexible segment of FIG. 2A.
Figure 2A:
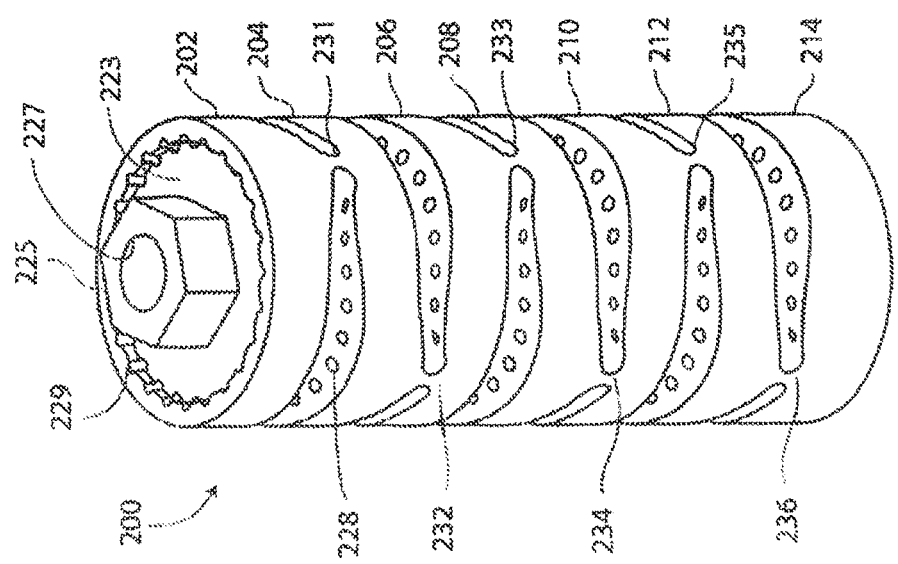
FIG. 2A is a perspective view of a flexible member according to another embodiment of the invention, with flexible segments having flexible hinges oriented orthogonal to one another.

Turning to FIGS. 2A-2C, flexible member 200 includes flexible segments 216, 218 and 220 formed by a series of links 202, 204, 206, 208, 210, 212 and 214 connected by flexible hinges 231, 232, 233, 234, 235 and 236, respectively. The flexible member terminates at either end at links 202 and 214. Terminal link 202 includes cylindrical recess 223 and hexagonal boss 225 facing away from terminal link 214. Terminal link 214, in turn includes hexagonal socket 224 facing away from terminal link 202. As depicted, flexible hinges 231, 233 and 235 are oriented orthogonal to flexible hinges 232, 234 and 236. As shown, the links further include channels 228 that receive the individual cables sets that control the links. The member is designed such that the cables will pass through cable channels in the links and terminate and be affixed to terminal link 202 of flexible segment 216. Specifically, the cables can exit channels 228 at exit points 229 and be affixed to recess 223 of link 202. Flexible segment 216 then acts as an active flexible segment with the remaining flexible segments being spacer flexible segments. Alternatively, a cable set could terminate any one of the other flexible segments, making any other flexible segment an active flexible segment. Also, while cable channels 228 are shown arranged in a circular pattern, such a pattern is not critical, as each channel can be located at any radial location along the member. Center channel 227 extends axially through the flexible member to accommodate additional elements of any tools or instrument associated with the flexible member or with any articulating mechanism that includes the flexible member. Alternatively, a similar channel could be provided at any other radial location along the member, including its perimeter. The flexible member can be incorporated into or form all of or a portion of the proximal and distal ends of an articulating mechanism according to the invention.

The flexible hinge system has a variety of important advantages. One is ease of manufacture and assembly, as the flexible segments, flexible members, or the articulating mechanism or portions thereof can be manufactured as single continuous piece having multiple links connected by the flexible hinges. In addition, multiple flexible segments or members of the same or differing configurations can be readily connected together to create a wide variety of articulating mechanisms, the characteristics of which will depend in part on the component flexible segments or members used. In the embodiment depicted in FIGS. 2A-2C, the reciprocating boss 225 and socket 224 allow multiple flexible members to be connected to each other, but one of skill in the art will appreciate there are a variety of reciprocating structures that can achieve the same purpose. A further advantage provided by the flexible hinge system is an increased ability to transmit torque along the mechanism. In mechanisms having individual links that are connected only by the cable sets, torque is less easily transmitted, as the force applied will cause some degree of twisting of the cables. Also, the flexible hinge systems allow the application of an axial load along the mechanism without compromising actuation. Articulation of the mechanism remains smooth and facile even under axial load. This is not the case in some other mechanisms where individual links are in frictional contact with one another and where an axial load increases frictional forces between the links, which causes a restriction in movement or in some cases cause the links to "lock up" entirely.

To achieve the greatest freedom of motion, at least one flexible hinge of the mechanism, flexible member or flexible segment is oriented orthogonal to at least one of the other flexible hinges. However, in applications where a more limited freedom of motion is acceptable, the flexible hinges need not be orthogonal. In the depicted embodiments of FIGS. 1-2, consecutive hinges are orthogonal to one another but the invention contemplates other configurations, including configurations where two or more consecutive hinges are oriented parallel to each other or are offset from each other anywhere from 0-90 degrees.

Turning to FIGS. 3-5, embodiments of flexible segments are depicted where the flexible hinges bend or flex at predetermined positions relative to the adjacent connected links. The links otherwise have the same overall diameter, the same diameter or distance between cable channels, and the same gap between the links. When incorporated into an articulating mechanism, the predetermined flex location between the links can have a positive, neutral or negative effect, or bias, on the relative tautness of cables passing through the link. More particularly, when a flexible segment bends due to an actuating force applied by a cable or cables along one side of the links of a segment, the relative tautness of cables passing through the other side of the links can be affected in a positive, negative or neutral manner. This effect, or bias, can also be referred to as "cable pull bias." Flexible segments that create or increase cable tension when the segment links are articulated are said to have "positive bias." Alternatively, flexible segments that result in decreased cable tension or slack when the segment links are articulated are referred to as having a "negative bias." Flexible segments that minimize cable tension and cable slack are said to have "neutral bias." Depending on the application, such positive, neutral or negative effects can be advantageous. The particular predetermined flex locations to achieve positive, neutral or negative cable pull bias will depend on the particular dimensions of a given pair of links and the connecting hinge or hinges, including the diameter of the cable channel pattern, the gap between the links where cables are exposed, and the maximum flex angle of the links. These particular predetermined flex locations can be measured as a particular offset (positive or negative) relative to the link surface where the cables emerge or exit from the cable channels. In operation, when the links of a flexible segment are manipulated into a desired position or configuration, the flexible hinge between two given links flexes or bends, such that the two links are flexing or bending toward or away from one another about the hinge. Under a neutral bias configuration, the distance a given cable channel exit point on one link moves towards its corresponding cable channel exit point on the other link is equal to the distance the opposing cable channel exit point on the opposite side of the link moves away from its corresponding cable channel exit point on the other link. The combined distance between the two respective sets of cable channel exit points, however, remains constant whether or not the segment is flexed, which is important to maintaining neutral cable bias. Where such combined distances are not equal, an increase in cable slack or tension can occur. Particularly, where the combined distance between sets of opposing channel exit points is greater when the links are flexed as compared to the combined distance in the straight, non-bent position, cable tension can occur. Alternatively, where the combined distance between sets of opposing channel exit points is lessened upon flexing or bending relative to a straight, non-bent position, cable slack can occur.

In the embodiment depicted in FIGS. 3A-3C, flexible segment 240 includes flexible hinge 246 connecting links 244 and 245. The links also include cable channels 248. The links have a cable channel pattern diameter of D, and are separated by gap G between the links where cables are exposed. The links have a maximum flex angle of G about hinge 246. In the situation where D is five times G, and T is 20 degrees, the desired predetermined flex position for neutral cable pull bias is an offset $O_1$ of {fraction ($1/100$)} D, which is practically at or near surface face 247 of link 245 where the cables emerge or exit from the cable channels. In other words, in this situation the flex position is aligned or nearly aligned with the surface portion of link 245 where the cables emerge or exit. In this particular configuration, cable slack is minimized over the range of motion of the segment. By minimizing cable slack, the mechanism can retain its shape over a range of motion and resist counter forces applied against the mechanism that would compromise shape accuracy. This will be advantageous in most applications. Configurations of flexible hinges that minimize slack in the cables are said to have a "neutral bias."

In the embodiment of FIGS. 4A-4C, flexible segment 260 has flexible hinge 266 with a predetermined flex position located between two adjoining links 264 and 265. Links 264 and 265 contain cable channels 268. In this configuration, the flexible hinge has a positive offset $O_2$ relative to the surface 267 of link 265. In the situation where dimensions D, G and T are as above, this flex position leads to a negative cable pull bias. That is, when the segment beads at these links due to an actuating force applied by a cable or cables along one side of the links there is typically slack created in the cable or cables along the opposite side of the links. In some applications, this creation of slack may be desirable as it will decrease the rigidity of the device in that area, and limit its resistance to counter forces deployed along that area. Examples where this could be desirable include navigation of the mechanism through or around sensitive or fragile anatomical structures. Flexible hinges that allow for some degree of slack in the cables are said to have a "negative bias."

The embodiment of FIGS. 5A-5C, flexible segment 280 includes flexible hinge 286 connecting links 284 and 285. Links 284 and 285 likewise include cable channels 288. In this configuration, the flex position has a negative offset $O_3$ relative to surface 287 of link 285. That is, the flex position is below the surface portion of link 285 where the cables emerge or exit. In the situation where dimensions D, G and T are as above, this flex position leads to a positive cable pull bias. That is, when the segment bends at these links due to an actuating force applied by a cable or cables along one side of the links there is typically tension created in the cable or cables along the opposite side of the links. In some applications, this creation of tension may be desirable as it will increase the rigidity of the device in that area and resist any applied counter force. Such tension can further provide a resistance to further bending of the mechanism, and provide feedback to the user. Examples where this could be desirable include applications where it is important to guard against too much bending or "overbending" of the mechanism. Flexible hinges having this configuration that create additional tension in the cables are said to have a "positive bias."

Figure 6:
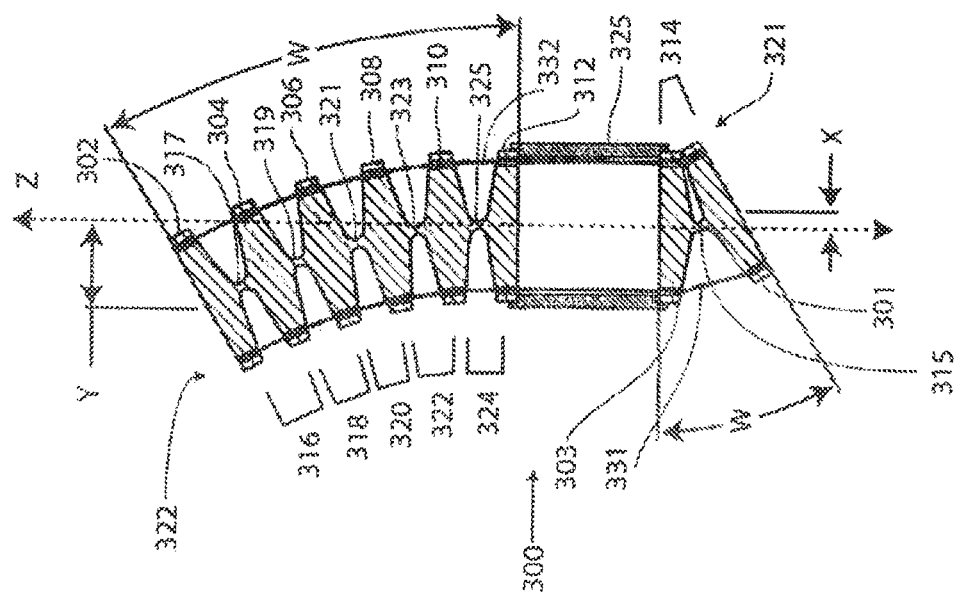
FIG. 6 is a side sectional view of an articulating mechanism according to another embodiment of the invention, showing a scaling of movement between the proximal and distal end.

FIG. 6 depicts another embodiment of the invention, with articulating mechanism 300 with proximal and distal ends 321, 322, respectively, and spacer element 325 disposed there between. Distal end 322 includes flexible segments 316, 318, 320, 322 and 324 formed by a series of links 302, 304, 306, 308, 310, and 312 connected by flexible hinges 317, 319, 321, 323, and 325, respectively. Proximal end 321 includes flexible segment 314 formed by links 301 and 303 connected by flexible hinge 315. As depicted, the flexible hinges are all oriented parallel to one another along the longitudinal axis of the unactuated mechanism (as represented by axis Z). In this manner, the mechanism can provide for two-dimensional movement, but not three dimensional movement. The links further include channels that receive cables 331 and 332 that form the cable set that controls actuation of the mechanism. As above, the mechanism is designed such that the cables will pass through cable channels in the links. The cables are secured to distal terminal link 302 of flexible segment 316 and to proximal terminal link 301 of flexible segment 314. Flexible segments 316 and 314 thus act as an active flexible segment pair with the remaining flexible segments being spacer flexible segments.

FIG. 6 shows articulating mechanism 300 in an actuated or manipulated condition. As seen proximal flexible segment 314 at proximal end 321 has been flexed about an angle of W. Due to the addition of the spacer segments at distal end 322, the entire distal end flexes about the equivalent angle W, but the angle between each flexible segment is lessened such that the angles in the cumulative match angle W. However, the distance Y that distal end 322 travels relative to the original axis line Z of the mechanism, is proportionally greater than the distance X that distal end 321 travels relative to axis Z. This illustrates how the addition (or subtraction) of spacer segments can result in achieving same overall angle of bend but across a greater (or lesser) lateral distance.

Figure 7:
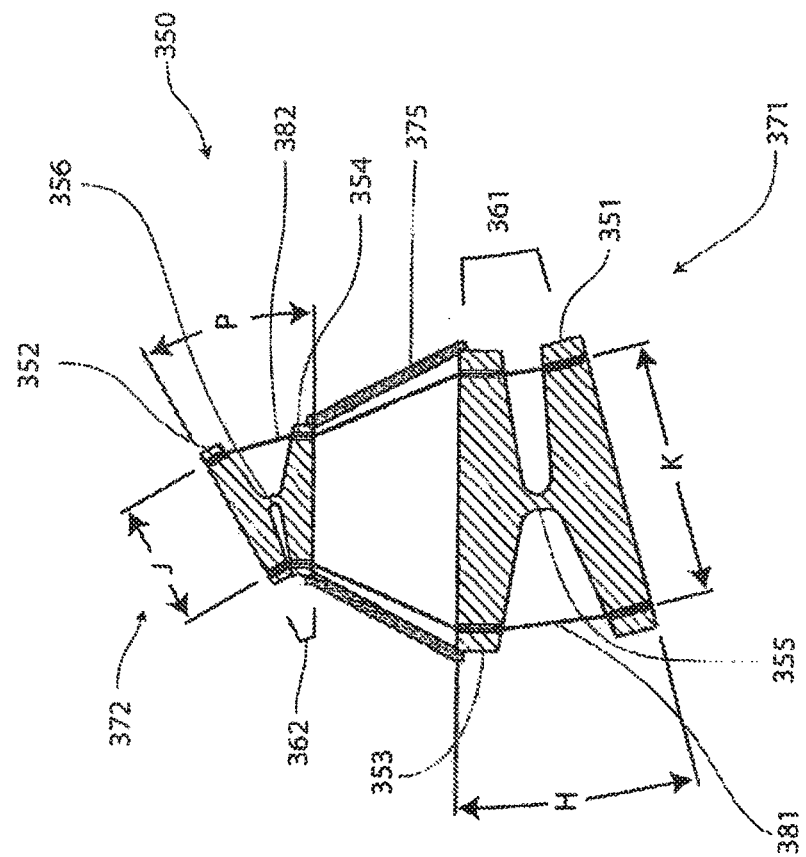
FIG. 7 is a side sectional view of an articulating mechanism according to yet another embodiment of the invention, showing a different scaling of movement between the proximal and distal end.

FIG. 7 depicts further embodiment of the invention, with articulating mechanism 350 having proximal and distal ends 371, 372, respectively separated by spacer element 375. Distal end 372 includes flexible segment 362 formed of links 352 and 354 connected by flexible hinge 356. Proximal end 371 includes flexible segment 361 formed by links 351 and 353 connected by flexible hinge 355. Again the flexible hinges are all oriented parallel to one another along the longitudinal axis (not shown) of the unactuated mechanism, again providing for two-dimensional movement, but not three dimensional movement. The links further include channels that receive cables 381 and 382 that form the cable set that controls actuation of the mechanism. Again, the mechanism is designed such that the cables will pass through cable channels in the links. The cables are secured to distal terminal link 352 of flexible segment 362 and to proximal terminal link 351 of flexible segment 361. Flexible segments 362 and 361 thus act as an active flexible segment pair. As depicted, the diameter K between cable channels of links 351 and 353 at the proximal end is larger than diameter J of corresponding links 352 and 354 at the distal end.

As shown, articulating mechanism 350 in an actuated or manipulated condition. As seen, proximal flexible segment 361 at proximal end 371 has been flexed about an angle of H. However the distal flexible segment 362 flexes about a larger angle of P. This is due to the change in diameter between cable channels between the proximal and distal links. The change in flex angle is generally proportional to the diameter differences, with angle P being proportional to angle H multiplied by the ratio of the two diameters (i.e., P.congment.H.times.(K/J)). For any two link pairs then, the difference can be expressed in terms of the resulting pivot angle that results when the links are manipulated relative to their unpivoted state. Thus, for any given link pair $L_1$ and $L_2$ having differing cable channel location radii of $R_1$ and $R_2$, respectively, from the center axis of the links and where $R_2 > R_1$, when $L_1$ is pivoted to an angle of $A_1$, corresponding link $L_2$ will have a resulting pivot angle $A_2 = A_1 \times \sin^{-1}(R_1/R_2)$. This illustrates how the increase or decrease of cable channel pattern diameter or radii can proportionally increase or decrease the angle of bend or flex in the mechanism. This can have important ergonomic applications, including in surgical applications where a smaller angle of flex at the user operating proximal end can result in a greater angle of flex or bend at the distal end, allowing for exaggerated or increased movement of the distal end to deploy and/or actuate surgical tools or instruments. In other applications it may be desirable for the user operating proximal end to have a larger angle of flex relative to the distal end.

Consistent with the above considerations, the links may further be of any size and shape, as the purpose dictates. For surgical applications, the size and shape of links usually depends on such factors as patient age, anatomy of the region of interest, intended application, and surgeon preference. Links are generally, but need not be, cylindrical, and as previously mentioned include channels for passage of the cables that connect the flexible segment pairs as well as additional cables, wires, fiberoptics or other like elements associated with a desired tool or instrument used in conjunction with the mechanism. The channel diameters are usually slightly larger than the cable diameters, creating a slip fit. Further, the links may also include one or more channels for receiving elements of attachable surgical instruments or diagnostic tools or for passage of cables that actuate them. The links may typically have a diameter from about 0.5 mm to about 15 mm or more depending on the application. For endoscopic applications, representative diameters may range from about 2 mm to about 3 mm for small endoscopic instruments, about 5 mm to about 7 mm for mid-sized endoscopic instruments, and about 10 mm to about 15 mm for large endoscopic instruments. For catheter applications, the diameter may range from about 1 mm to about 5 mm. Overall length of the links will vary, usually depending on the bend radius desired between links.

The articulating mechanism, flexible members and flexible segments may be formed of a number of materials known in the art and that can vary according to the application. For ease of manufacture, injection moldable polymers can be used including, e.g., polyethylene or copolymers thereof, polyethylene terephthalate or copolymers thereof, nylon, silicone, polyurethanes, fluoropolymers, poly (vinylchloride); and combinations thereof, or other suitable materials known in the art.

For surgical applications a lubricious coating may be placed on the links or segments if desired to facilitate advancement of the articulating mechanism. The lubricious coating may include hydrophilic polymers such as polyvinylpyrrolidone, fluoropolymers such as tetraflroethylene, or silicones. A radioopaque marker may also be included on one or more segments to indicate the location of the articulating-mechanism upon radiographic imaging. Usually, the marker will be detected by fluoroscopy.

Cable diameters vary according to the application. For surgical applications in general, cable diameters and may range from about 0.15 mm to about 3 mm. For catheter applications, a representative diameter may range from about 0.15 mm to about 0.75 mm. For endoscopic applications, a representative diameter may range from about 0.5 mm to about 3 mm.

Cable flexibility may be varied, for instance, by the type and weave of cable materials or by physical or chemical treatments. Usually, cable stiffness or flexibility will be modified according to that required by the intended application of the articulating mechanism. The cables may be individual or multi-stranded wires made from material, including but not limited to biocompatible materials such as nickel-titanium alloy, stainless steel or any of its alloys, superelastic alloys, carbon fibers, polymers, e.g., poly (vinylchloride), polyoxyethylene, polyethylene terephthalate and other polyesters, polyolefin, polypropylene, and copolymers thereof; nylon; silk; and combinations thereof, or other suitable materials known in the art.

The cables may be affixed to the flexible segments of an active pair according to ways known in the art, such as by using an adhesive or by brazing, soldering, welding, and the like, including methods described in pending and co-owned U.S. application Ser. Nos. 10/444,769 and 10/928,479, incorporated herein by reference in their entirety.

Although the many articulating mechanisms and flexible members that have been illustrated in the accompanying figures have a certain number of flexible segments and flexible segment pairs, this is solely for the illustrative purpose of indicating the relationship of the individual mechanism or flexible segment components to one another. Any number of flexible segments and flexible segment pairs may be employed, depending on such factors as the intended use and desired length of the articulating mechanism.

The natural configuration of the articulating mechanisms, flexible members or flexible segments is usually linear, although if desirable the mechanisms, flexible members or flexible segments can be manufactured to have a preformed bend. If maintenance of a certain curvature or other complex configuration is desired at the distal end of the articulating mechanism, the mechanism can be "locked" into place according to ways described e.g. in pending and co-owned U.S. application Ser. Nos. 10/444,769 and 10/928,479, incorporated herein by reference in their entirety. For example, a malleable tube slidable over the proximal segments may be shaped to keep the proximal segments, and thus, their corresponding distal segments in a particular configuration. This may be advantageous where, for example, a user has navigated the mechanism to a desired target location and wishes to "lock" the mechanism in place while e.g. actuating a tool associated with the mechanism, or engaging in a separate procedure altogether. By the term "malleable" it is meant that the tube is flexible enough so that it is capable of being shaped, but rigid enough so that it maintains its shaped form. In another variation, a locking rod may be inserted into one or more attachment channels extending through the flexible segments or segments to "lock" the proximal and distal segments of the articulating mechanism in place. The locking rod may be a malleable metal bar that may be shaped and then inserted into the attachment channels to set the proximal and distal segments into a particular configuration, or the locking rods may be provided in preshaped forms. In a further variation, the flexible segments or members themselves may be formed of a malleable material that retains its shape once manipulated into the desired configuration.

As noted, the articulating mechanisms of this invention may be used to direct a surgical or diagnostic instrument tool within a body region or to a target site within a body region of a patient either in its native, straight configuration, or after undergoing various manipulations at its proximal end from a location outside the patient. After appropriate insertion, movement of the proximal end of the mechanism, results in reciprocal movement at the distal end. Further, the resulting directional movement of the distal end can be inverted, mirrored or otherwise, depending on the degree of rotation of the proximal and relative to the distal end. Also, the proximal end provides for a user interface to control the steering and manipulation of the distal end that is convenient and easy to use relative to other conventional steering mechanisms that rely on e.g., pulleys or knobs to control steering wires. This user interface allows for example a user to readily visualize the shape and directional movement of distal and of the mechanism that is located e.g. within a patient based on the manipulated shape of the externally positioned proximal end user interface. In a further variation, the flexible segments or members themselves may be formed of a malleable material that retains its shape once manipulated into the desired configuration.

The articulating mechanism may be employed for remote manipulation of surgical instruments, diagnostic tools, various catheters, and the like, into hollow or chambered organs and/or tissues including, but not limited to, blood vessels (including intracranial vessels, large vessels, peripheral vessels, coronary arteries, aneurysms), the heart, esophagus, stomach, intestines, bladder, ureters, fallopian tubes, ducts such as bile ducts, and large and small airways. The articulating mechanism may also be used to remotely direct surgical instruments, diagnostic tools, various catheters, and the like, to solid organs or tissues including, but not limited to, skin, muscle, fat, brain, liver, kidneys, spleen, and benign or malignant tumors. The articulating mechanism may be used in mammalian subjects, including humans (mammals include, but are not limited to, primates, farm animals, sport animals, cats, dogs, rabbits, mice, and rats).

Turning to FIGS. 8-12, an embodiment of the invention is depicted which incorporates an articulating mechanism with flexible segments into a surgical instrument. FIG. 8A illustrates a surgical grasping instrument 400 which includes an elongate shaft 405 which separates proximal and distal flexible members 406 and 407, respectively. The flexible members are as described above, with multiple cables associated with discrete flexible segments such that movement of the proximal end results in corresponding movement of the distal end. Actuating handle 402 is located at the proximal end of proximal flexible member 406, and has a standard ratchet handle interface with pivoting arms 403 and 404 that are pivotable toward and away from one another. The distal end of arm 403 is fixedly secured to the proximal end of proximal flexible member 406. Grasping tool 410 is attached at the distal end of distal flexible member 407. As more clearly shown in FIG. 8B, grasping tool 410 includes upper and lower jaws 412 and 414 that are connected to jaw housing 416, with base 418 of housing 416 being fixedly secured to the distal end of distal flexible member 407.

More particularly, jaw housing 416 includes opposed parallel extending walls 420 and 422 with the proximal ends of jaws 412 and 414 positioned between the walls. As seen most clearly in FIGS. 8B-11B, each jaw includes slots that receive pins that span the space between the two walls. Specifically, upper jaw 412 includes slots 452 and 456 that receive pins 423 and 424, respectively. Lower jaw 414 includes slots 454 and 458 that receive pins 425 and 426. The slots of each jaw are oriented at an angle relative to the distal grasping portion of the jaws and are generally parallel to one another over most of the length of each slot. As can be seen however with particular reference to FIGS. 10B and 11B, both slots 452 and 454 have proximal terminal portions 453 and 455 respectively that diverge from parallel relative to respective slots 456 and 458. This will have an important impact on jaw movement as further discussed below. Jaws 412 and 414 also include notches 457 and 459, with notch 457 located between slots 452 and 456 on jaw 412 and notch 459 located between slots 454 and 458 on jaw 414. These notches 457 and 459 accommodate pins 424 and 426, respectively, when the jaws are in the closed position (see FIG. 9B). Jaws 412 and 414 are also pivotally connected to link arms 436 and 438, respectively, which in turn are pivotally connected at their other ends to cable terminator 430, which likewise resides within housing 416 and between walls 420 and 422. Actuating cable 432 is connected to and terminates at cable terminator 430 with cable 432 itself extending proximally through the jaw housing 416 and through a central channel (not shown) that extends through flexible member 407, elongate shaft 405, and terminates at its other end at arm 404 of handle 402. Bias spring 434 is aligned axially with cable 432 and is disposed between cable terminator 430 and base 418 of jaw housing 415. Jaws 412 and 414 themselves include opposing jaw surfaces 442 and 444, respectively. The jaw surfaces are each provided with channels 446 and 448 respectively that can receive e.g. an energy source suitable for ablating tissue.

The configuration of the jaw and jaw housing connection provides important advantages as it allows for parallel movement of the jaws over a first range of motion while further allowing for the jaws to diverge in a non-parallel fashion over a second range of motion. This overall range of motion can be observed by reference to FIGS. 9-11, with the jaws able to move from a closed position (FIGS. 9A-9B) to a first open position (FIGS. 10A-10B) while remaining parallel to each other et all times during such movement. Prom this first open position, the jaws can then move in a non-parallel fashion to a second open position (FIGS. 11A-11B). In this second open position, the distal tips of the jaws have diverged further from one another relative to the proximal ends of the jaws, creating a larger opening between the jaws at the tips, similar to what occurs with jaws that are connected by a single pivot. This larger opening is advantageous as it facilitates navigating the jaws around target tissue or anatomy. At the same time, the jaws maintain a parallel movement relative to each other upon closing from the first open position (FIGS. 10A-10B) to the closed position (FIGS. 9A-9B), which provides a variety of advantages, including an even force distribution across the jaws as they are closed upon target tissue. In addition, where an energy source is attached to the jaws for e.g. ablation, the parallel movement of the jaws allows for a more uniform transfer of energy to the tissue along the length of the jaws, providing more uniform and consistent ablation.

This overall range of motion is achieved as follows. As can be seen, bias spring 434 is positioned to continually bias the jaws apart from each other in the open position. The spring bias can be overcome by actuating handle 402 to translate cable 432 and connected cable terminator 430 toward the proximal end of the instrument, bringing the jaws into the closed position depicted in FIGS. 9A-9B. As tension on the cable is released, the jaws are biased open from the closed position to the first open position (FIGS. 10A-10B), the jaws remain parallel as upper and lower jaws 412 and 414 translate in directions parallel to slots 452, 456 and 454, 458, respectively, as slots 452, 456 and 454, 458 translate relative to pins 423, 424 and 425, 426, respectively. During this range of motion, the terminal ends of link arms 436 and 438 that are coupled to cable terminator 430 also translate, but any force exerted by the link arms that would result in non-parallel movement is overcome by the restraining force of pins 423, 424 and 425, 426 retained in parallel slots 452, 456 and 454, 458, respectively. However, as the jaws are further biased open, pins 423 and 425 relatively translate into the terminal portions 453 and 455 of slots 452 and 454, respectively, which diverge from parallel relative to respective slots 456 and 458. Relative movement of the pins into these non-parallel portions allows link arms 436 and 438 to pivot as well as translate, resulting in the divergent movement of jaws 412 and 414 relative to each other as the jaws move to the second open position (FIGS. 11A-11B).

In yet a further variation, the articulating mechanism and flexible segments of the invention can be incorporated into a catheter and used to guide the catheter. As shown in FIGS. 16A and 16B, catheter 700 incorporates an articulating mechanism with the distal end of the mechanism 702 integral with the distal end of the catheter, and the proximal end formed of flexible member 704 extending from handle 706. Proximal end flexible member 704 is formed of flexible segments 711, 713 and 715 similar to those described herein. Distal end sections 712, 714, and 716 are integrally formed sections of the distal end 702 of the catheter. Cable sets (not shown) connect distal end sections 712, 714, and 716 to proximal end segments 711, 713 and 715, such that distal and 702 can be remotely maneuvered by manipulating proximal end flexible member 704 in order to guide the catheter 700 as it is advanced. As seen more clearly in FIG. 16B, the distal end of catheter 700 includes a catheter tube with a central lumen 724 and multiple cable channels 728 that extend the length of the catheter and that can receive cable sets (not shown) that connect the distal and proximal segments. The central lumen can provide passage for e.g., wires, energy sources, or other control elements to the catheter tip, or function as through lumen for the passage of fluids, or can otherwise provide for known functions of catheter lumens. The cables can be anchored within the catheter tube at the desired locations as described in pending and co-owned U.S. application Ser. No. 10/444,769, incorporated herein by reference in its entirety. Each distal end segment of the catheter can be formed of material having a different durometer and/or can be of varying lengths, which can provide an additional level of control when manipulating the catheter. For example, if the distal-most section were of the lower durometer relative to the proximal most section, then control of the distal tip would be enhanced as less cable force would be required to articulate the distal-most section relative to the force required to articulate the proximal most section. In alternative embodiments, the distal end segments can be formed of discrete sections of catheter tube material that abut one another and which are maintained in position relative to one another by the passage and affixing of the cable sets within the sections. Further, while catheter 700 includes proximal end flexible member 704 formed of flexible segments as described herein, it is further contemplated that the proximal end can alternatively be formed of a wide variety of articulating link systems that are similarly connected to the distal end through cable sets. Such articulating link systems include, but are not limited to, those described in pending and commonly owned U.S. application Ser. Nos. 10/444,769 and 10/928,479, incorporated herein by reference in their entirety.

Figure 12:
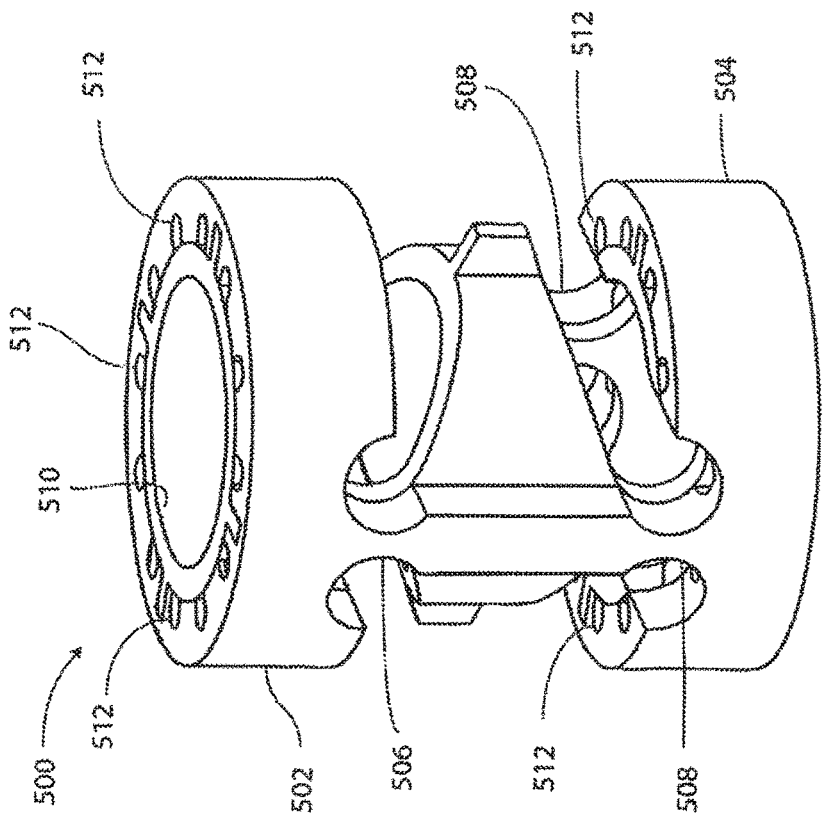
FIG. 12 is a perspective view of a flexible segment of yet another embodiment of the invention.
Figure 13:
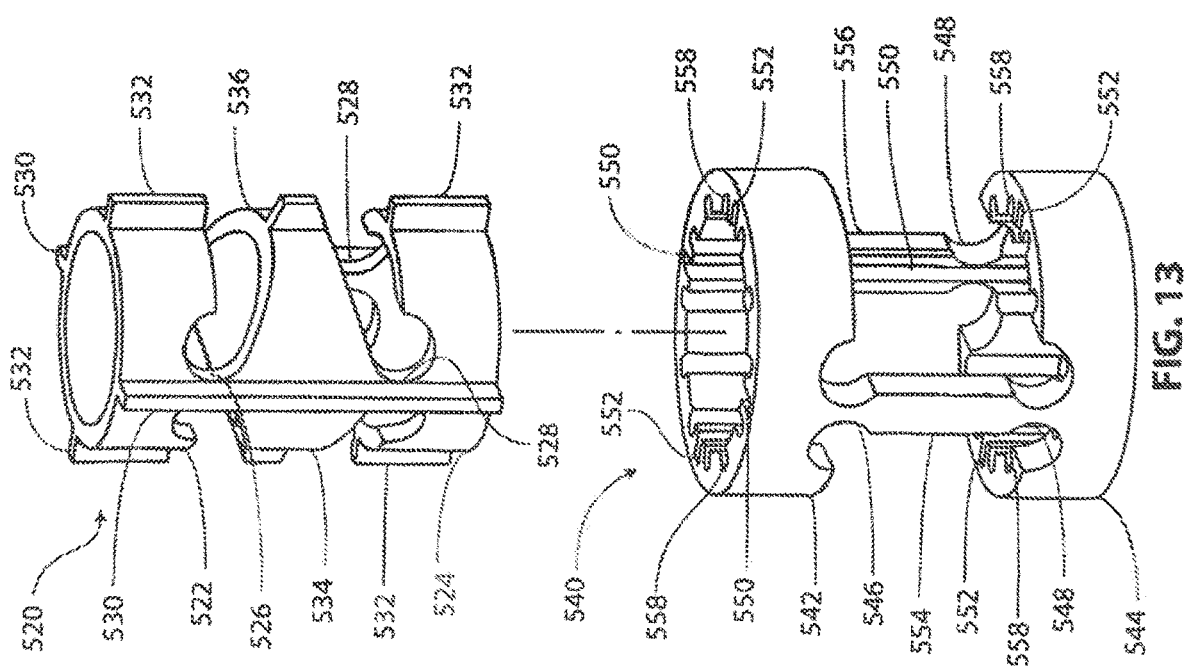
FIG. 13 is an exploded view of the flexible segment of FIG. 12, showing the inner core and outer cover that form the flexible segment of FIG. 12.

FIGS. 12-13 depict a flexible segment according to another embodiment of the invention. As shown in FIG. 12, flexible segment 500 includes two flexible hinges 506 and 508 that connect links 502 and 504, and otherwise shares many features of the previously described flexible segments. Cable channels 512 are provided for passage and receipt of cables for controlling the segment itself or other segments. Central channel 510 is also provided. As more particularly shown in FIG. 13, flexible segment 500 is formed of two components, inner core 520 and outer cover 540. The provision of a flexible segment formed of inner core and outer cover components provides manufacturing advantages, as will be further described. Inner core 520 is configured to be received axially within outer cover 540. Inner core 520 includes link sections 522 and 524 that are each generally cylindrical. Flexible hinge sections 526 and 528 connect each link section to wing sections 534 and 536 which together form another generally cylindrical portion aligned with and disposed between the two link sections, and which when combined with the link sections provide for central channel 510 of the formed flexible segment 500. The inner core also includes alignment flanges 530 and 532 that extend lengthwise along the outer surface of the core. Outer cover 540 likewise includes link sections 542 and 544 that are also generally cylindrical. Flexible hinge section 546 and 548 connect each link section to stem sections 554 and 556 which are aligned with and disposed between the two link sections. Extending lengthwise along the interior surface of outer cover 549 is a series of cable slots 558. The outer cover 540 also includes alignment slots 550 and 552 that extend lengthwise along the interior surface of the cover, with slots 550 in particular extending along stems sections 554 and 556. These slots receive alignment flanges 530 and 532 respectively of inner core 520, such that when the inner core and outer cover are assembled together, the respective link sections and flexible hinge sections of the inner core and outer cover are in alignment with each other to form the links and flexible hinges of the formed flexible segment 500, as well as forming cable channels 512. Specifically, link sections 522 and 542 form link 502, flexible hinge sections 526 and 546 form flexible hinge 506, flexible hinge sections 528 and 548 form flexible binge 508, and link sections 524 and 544 form link 504. The outer surface of inner core 520 abuts the inner surface of outer cover 540, sealing off cable slots 558 lengthwise, and thereby forming cable channels 512.

For flexible segments and members formed through molding processes, the manufacture of an inner core and outer cover components can be simpler and more economical process than manufacturing the flexible segments or members as a single component. For example, molding flexible segments having cable channels as a single component requires the use of many small core-pins that run the entire length of the part as part of molding process. Molding outer cover components with cable slots is a simpler process, with the mold cavity itself providing for the slots. Further, while the depicted embodiment of FIGS. 12-13 is a dual or double flex hinge link segment, it can be easily appreciated that a wide variety of flexible hinge links, segments, and flexible members can be formed from inner core and outer cover components, including but not limited to the other links, segments and members described herein. Additionally, other links and link systems can similarly be formed of inner core and outer cover components.

The particular configuration of flexible segment 500 also achieves other advantages. In particular, the dual hinge configuration of flexible segment 500 also provides for neutral cable bias, similar to the fashion provided by neutral cable bias dual-pivoting link systems described in pending and commonly owned U.S. application Ser. No. 10/928,479, incorporated herein by reference in its entirety. With reference to FIG. 12, it can be appreciated that flexible hinges 506 and 508 or flex or bend at locations that generally coincide with opposing faces of each link 502 and 504, and thus further coincide with cable channel exit points where actuating cables would exit from each respective link. When the flexible segment is manipulated into a desired position or configuration, each flexible hinge flexes or bends, such that the two links are flexing or bending toward or away from one another about the dual hinges. Further, as a result of such dual flexing action, the distance a given cable channel exit point on one link moves towards its corresponding cable channel exit point on the other link is equal to the distance the opposing cable channel exit point on the opposite side of the link moves away from its corresponding cable channel exit point on the other link, similar to neutral cable bias flexible segments described above. The combined distance between the two respective sets of cable channel exit points, however, remains constant whether or not the segment is flexed, which is important to maintaining neutral cable bias. Where such combined distances are not equal, an increase in cable slack or tension can occur. Particularly, where the combined distance between sets of opposing channel exit points is greater when the links are flexed as compared to the combined distance in the straight, non-bent position, cable tension can occur. Alternatively, where the combined distance between sets of opposing channel exit points is lessened upon flexing or bending relative to a straight, non-bent position, cable slack can occur.

Other advantages offered by the configuration of flexible segment 500 include wing sections 536 and 534, which can function as stops to prevent overflexing of the hinge regions. When flexible segment 500 is bent or flexed, opposing sides of links 502 and 504 will move toward each other until they contact one or the other wing section, restricting further bending movement. So for example, for a flexible segment designed for a total maximum bend angle of 60 degrees, the wing sections would be configured to limit each flexible hinge to a maximum of 30 degrees. This is illustrated more clearly with reference to FIGS. 14-15, which depict flexible segment 600, which is similar to flexible segment 500 but is of single unit construction. Similar to flexible segment 500, flexible segment 600 includes two links 602 and 604 connected by flexible hinges 606 and 608. Cable channels 612 are provided for passage and receipt of cables and central channel 610 is also provided. More specifically, flexible hinges 606 and 608 connect links 602 and 604, respectively, to wing sections 624 and 626 disposed between and aligned with the two links. Stem sections 614 and 616, which extend longitudinally from the wing sections, are also connected to and aligned with links 602 and 604. As depicted most clearly in FIG. 15B, wing section 624 acts as a stop to limit further bending of flexible segment 600.

The invention also contemplates kits for providing various articulating mechanisms and associated accessories. For example, kits containing articulating mechanisms having different lengths, different segment diameters, and/or different types of tools or instruments may be provided. The kits may optionally include different types of locking rods or malleable coverings. The kits may be further tailored for specific applications. For example, kits for surgical application can be configured for, e.g., endoscopy, retraction, or catheter placement, and/or for particular patient populations, e.g., pediatric or adult.

All publications, patents, and patent applications cited herein are hereby incorporated by reference in their entirety for all purposes to the same extent as if each individual publication, patent, or patent application were specifically and individually indicated to be so incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit and scope of the appended claims.

What is claimed is:

1. A surgical clamp comprising:
   a pair of opposing jaws moveable relative to each other between a closed position and first and second open positions, the opposing jaws remaining substantially parallel to one another when moving between the closed position and the first open position and remaining non-parallel to one another when moving between the first open position and the second open position.

2. The surgical clamp of claim 1, wherein each of the opposing jaws includes first and second slots that receive first and second pins that extend from a jaw housing, and wherein the first and second slots are parallel to one another over a first length of each slot and are non-parallel to one another over a second length of each slot.

3. The surgical clamp of claim 2, wherein as the pair of opposing jaws moves from the closed position to the first open position, each opposing jaw translates in a direction substantially parallel to the first length of the first and second slots of each opposing jaw, respectively.

4. The surgical clamp of claim 2, wherein as the pair of opposing jaws moves from the first open position to the second open position, the first pin of each opposing jaw translates into a terminal portion of the first slot of each opposing jaw, respectively.

5. The surgical clamp of claim 1, wherein opposing jaw surfaces of the pair of opposing jaws each include channels for receiving an energy source.

6. The surgical clamp of claim 1, wherein in the closed position, a gap is maintained between the pair of opposing jaws.

7. The surgical clamp of claim 1, wherein in the second open position, a distance between a distal tip of each of the opposing jaws is greater than a distance between a proximal end of each of the opposing jaws.

8. The surgical clamp of claim 1, wherein the opposing jaws remain substantially parallel to one another when moving between the first open position and the closed position.

9. The surgical clamp of claim 8, wherein a force is distributed substantially evenly across each of the opposing jaws as the pair of opposing jaws moves from the first open position to the closed position to close upon a target tissue.

10. The surgical clamp of claim 1, further comprising a spring, the spring being positioned to provide a biasing force to continually bias the pair of opposing jaws apart from one another in the second open position.

11. The surgical clamp of claim 10, wherein the biasing force can be overcome to bring the pair of opposing jaws into the closed position by actuating a handle to translate a cable and a cable terminator in a longitudinal direction toward a proximal end of the surgical clamp.

12. The surgical clamp of claim 11, wherein the spring is axially aligned with the cable.

13. The surgical clamp of claim 1, further comprising:
a first link arm; and
a second link arm,
wherein a terminal end of the first link arm is pivotally coupled to one jaw of the pair of opposing jaws, and wherein a terminal end of the second link arm is pivotally coupled to the other jaw of the pair of opposing jaws.

14. The surgical clamp of claim 13, wherein as the pair of opposing jaws moves from the closed position to the first open position, each terminal end of the first and second link arms translates in a direction substantially parallel to a first length of first and second slots of each opposing jaw, respectively.

15. The surgical clamp of claim 14, wherein a proximal end of the first link arm and a proximal end of the second link arm are pivotally coupled to a cable terminator of the surgical clamp at a same point.

16. The surgical clamp of claim 15, wherein as the pair of opposing jaws moves from the first open position to the second open position,
the first and second link arms translate in a direction substantially parallel to the first length of the first and second slots of each opposing jaw, respectively, and
the first and second link arms pivot about the same point where the proximal ends of the first and second link arms are pivotally coupled to the cable terminator.

* * * * *